United States Patent
Deroover et al.

(10) Patent No.: US 7,812,113 B2
(45) Date of Patent: *Oct. 12, 2010

(54) PHENYLAZO-ACETOACETANILIDE DERIVATIVES WITH A POLYMERIZABLE FUNCTIONAL GROUP AND RELATED COMPOUNDS AS MONOMERS FOR PREPARING POLYMERIC PIGMENT DISPERSANTS FOR INKJET INKS

(75) Inventors: Geert Deroover, Lier (BE); Wojciech Jaunky, Wesel (DE); Lambertus Groenendaal, Sinaai (BE); Johan Loccufier, Zwijnaarde (BE)

(73) Assignee: Agfa Graphics NV, Mortsel (BE)

( * ) Notice: Subject to any disclaimer, the term of this patent is extended or adjusted under 35 U.S.C. 154(b) by 411 days.

This patent is subject to a terminal disclaimer.

(21) Appl. No.: 11/995,329

(22) PCT Filed: Jul. 4, 2006

(86) PCT No.: PCT/EP2006/063829

§ 371 (c)(1),
(2), (4) Date: Jan. 11, 2008

(87) PCT Pub. No.: WO2007/006682

PCT Pub. Date: Jan. 18, 2007

(65) Prior Publication Data

US 2008/0177016 A1    Jul. 24, 2008

Related U.S. Application Data

(60) Provisional application No. 60/713,437, filed on Sep. 1, 2005.

(30) Foreign Application Priority Data

Jul. 14, 2005    (EP)    .................... 05106460

(51) Int. Cl.
C08G 73/00    (2006.01)
C07C 251/00    (2006.01)
C07C 241/00    (2006.01)
C07C 257/00    (2006.01)
C07C 243/10    (2006.01)
C07C 291/00    (2006.01)
C07C 249/00    (2006.01)
C08L 39/00    (2006.01)
C08F 2/22    (2006.01)
C08F 2/20    (2006.01)
C08K 3/00    (2006.01)
C09D 11/00    (2006.01)

(52) U.S. Cl. ............. 528/367; 564/248; 564/250; 564/249; 524/543; 524/555; 524/804; 524/827; 524/80; 523/161

(58) Field of Classification Search ............ 564/248, 564/249, 250; 522/10; 524/543, 555, 804, 524/827, 80
See application file for complete search history.

(56) References Cited

U.S. PATENT DOCUMENTS 2,976,294 A * 3/1961 Firestine ............. 548/369.7
4,489,197 A    12/1984    Wang et al.
4,664,709 A    5/1987    Castenson
5,367,039 A    11/1994    Yabuuchi et al.
5,420,187 A    5/1995    Endo et al.
5,859,133 A    1/1999    Zanzig et al.
7,582,150 B2*    9/2009    Jaunky et al. ............ 106/31.52
7,582,151 B2*    9/2009    Jaunky et al. ............ 106/31.52
7,582,152 B2*    9/2009    Jaunky et al. ............ 106/31.52
2003/0044707 A1    3/2003    Itabashi
2004/0194665 A1    10/2004    Konemann et al.

FOREIGN PATENT DOCUMENTS

| CA | 2 157 361 C | 9/1994 |
| EP | 0 763 378 A1 | 3/1997 |
| EP | 0 763 580 A2 | 3/1997 |
| EP | 1 182 218 A1 | 2/2002 |
| EP | 1 245 644 A2 | 10/2002 |
| EP | 1 491 592 A2 | 12/2004 |
| GB | 1 343 606 | 1/1974 |
| GB | 1 424 517 | 2/1976 |
| JP | 7-41693 A | 2/1995 |
| JP | 2003-96191 A | 4/2003 |
| JP | 2004-2529 A | 1/2004 |
| WO | 00/20476 A1 | 4/2000 |
| WO | 02/42282 A2 | 6/2002 |
| WO | 2005/056692 A2 | 6/2005 |
| WO | 2005/056693 A1 | 6/2005 |

OTHER PUBLICATIONS

Nippon Kagaku Kaishi, 1977, 9, p. 1369-1372.*

(Continued)

*Primary Examiner*—Vasu Jagannathan
*Assistant Examiner*—Karuna P Reddy
(74) *Attorney, Agent, or Firm*—Keating & Bennett, LLP

(57) ABSTRACT

A monomer with a chromophore group represented by Formula (I):

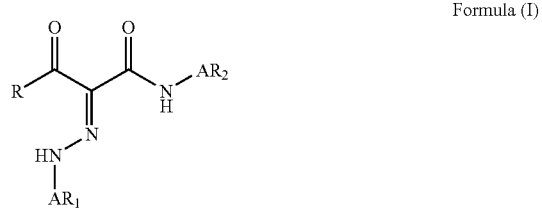

Formula (I)

wherein
$AR_1$ represents a substituted or unsubstituted aromatic group;
$AR_2$ represents a substituted or unsubstituted aromatic group or a substituted or unsubstituted alkyl group;
and R represents a substituted or unsubstituted alkyl group, with the proviso that one of R, $AR_1$, and $AR_2$ has a substituent with a polymerizable functional group. The monomer can be advantageously used to prepare polymeric dispersants for pigment dispersion, especially inkjet inks.

10 Claims, No Drawings

OTHER PUBLICATIONS

Official communication issued in counterpart International Application No. PCT/EP2006/063829, mailed on Oct. 20, 2006.

Wojciech Jaunky et al.: "Pigment Dispersions With Polymeric Dispersants Having Pending Chromophore Groups," U.S. Appl. No. 11/995,325, filed Jan. 11, 2008.

Johan Loccufier et al.: "Pigment Dispersions With Polymeric Dispersants Having Pending Chromophore Groups," U.S. Appl. No. 11/995,328, filed Jan. 11, 2008.

Geert Deroover et al.: "Pigment Dispersions With Polymeric Dispersants Having Pending Chromophore Groups," U.S. Appl. No. 11/995,321, filed Jan. 11, 2008.

Wojciech Jaunky et al.: "Pigment Dispersions With Polymeric Dispersants Having Pending Chromophore Groups," U.S. Appl. No. 11/995,323, filed Jan. 11, 2008.

Wojciech Jaunky et al.: "Pigment Dispersions With Polymeric Dispersants Having Pending Chromophore Groups," U.S. Appl. No. 11/995,322, filed Jan. 11, 2008.

Johan Loccufier et al.: "Pigment Dispersions With Polymeric Dispersants Having Pending Chromophore Groups," U.S. Appl. No. 11/995,330, filed Jan. 11, 2008.

Breitfelder et al.: "Synthesis of Pederic Acid and Related Model Studies," Helvetica Chimica Acta, vol. 87, No. 5, 2004; pp. 1202-1213.

Khudina et al.: "Fluoroalkyl-Containing 2-Arylhydrazono-1, 3-Dicarbonyl Compounds in the Reactions With Ehylenediamine and Polyethylenepolyamines," Journal of Flourine Chemistry, vol. 125, No. 3, 2004; pp. 401-407.

Hein et al.: "New Pigments From 3,3?-Dichloro-and 3,3?-Dimethoxy-4, 4?-Diaminostilbene," Journal of the American Chemical Society, vol. 77, No. 15, 1955, pp. 4107-4109.

Database Beilstein, "2-[m-methacrylmidophenyl)-azo]-acetoacet anilid," XP002389900, Database Accession No. BRN: 1828719, Abstract (citing: Inukai et al.: "Nippon Kagaku Kaishi," 1977).

* cited by examiner

PHENYLAZO-ACETOACETANILIDE DERIVATIVES WITH A POLYMERIZABLE FUNCTIONAL GROUP AND RELATED COMPOUNDS AS MONOMERS FOR PREPARING POLYMERIC PIGMENT DISPERSANTS FOR INKJET INKS

CROSS-REFERENCE TO RELATED APPLICATIONS

This application is a 371 of PCT/EP2006/063829, filed Jul. 4, 2006. This application claims the benefit of U.S. Provisional Application No. 60/713,437, filed Sep. 1, 2005, which is incorporated herein by reference in its entirety. In addition, this application claims the benefit of European Application No. 05106460.8, filed Jul. 14, 2005, which is also incorporated herein by reference in its entirety.

BACKGROUND OF THE INVENTION

1. Field of the Invention

The present invention relates to monomers having chromophore groups that exhibit a structural similarity with a color pigment in a pigment dispersion and a pigmented inkjet ink.

2. Description of the Related Art

Pigment dispersions are made using a dispersant. A dispersant is a substance for promoting the formation and stabilization of a dispersion of pigment particles in a dispersion medium. Dispersants are generally surface-active materials having an anionic, cationic, or non-ionic structure. The presence of a dispersant substantially reduces the required dispersing energy. Dispersed pigment particles may have a tendency to re-agglomerate after the dispersing operation due to mutual attraction forces. The use of dispersants also counteracts this re-agglomeration tendency of the pigment particles.

The dispersant has to meet particularly high requirements when used for inkjet inks. Inadequate dispersing manifests itself as increased viscosity in liquid systems, loss of brilliance, and/or hue shifts. Moreover, particularly good dispersion of the pigment particles is required to ensure unimpeded passage of the pigment particles through the nozzles of the print head, which are usually only a few micrometers in diameter. In addition, pigment particle agglomeration and the associated blockage of the printer nozzles has to be avoided during the standby periods of the printer.

Polymeric dispersants contain in one portion of the molecule so-called anchor groups, which adsorb onto the pigments to be dispersed. In a spatially separate portion of the molecule, polymeric dispersants have polymer chains sticking out whereby pigment particles are made compatible with the dispersion medium, i.e., are stabilized.

The properties of polymeric dispersants depend on both the nature of the monomers and their distribution in the polymer. Polymeric dispersants obtained by randomly polymerizing monomers (e.g., monomers A and B polymerized into ABBAABAB) or by polymerizing alternating monomers (e.g., monomers A and B polymerized into ABABABAB) generally result in a poor dispersion stability. Improvements in dispersion stability have been obtained using graft copolymer and block copolymer dispersants.

Graft copolymer dispersants consist of a polymeric backbone with side chains attached to the backbone. CA 2157361 (DU PONT) discloses pigment dispersions made by using a graft copolymer dispersant with a hydrophobic polymeric backbone and hydrophilic side chains.

Block copolymer dispersants containing hydrophobic and hydrophilic blocks have been disclosed in numerous inkjet ink patents.

U.S. Pat. No. 5,859,113 (DU PONT) discloses an AB block copolymer dispersant with a polymeric A segment of polymerized glycidyl(meth)acrylate monomers reacted with an aromatic or aliphatic carboxylic acid, and a polymeric B segment of polymerized alkyl(meth)acrylate monomers having 1-12 carbon atoms in the alkyl group, hydroxy alkyl (meth)acrylate monomers having about 1-4 carbon atoms in the alkyl group.

In the design of polymeric dispersants for aqueous inkjet inks, the above mentioned anchor groups, which adsorb onto the pigments to be dispersed, are generally hydrophobic groups exhibiting an affinity for the pigment surface.

EP 0763580 A (TOYO INK) discloses an aqueous type pigment dispersing agent having a portion which has a high affinity with a pigment and which has at least one type selected from the group consisting of an organic dye, anthraquinone, and acridone only at a terminal end or at both terminal ends of at least one aqueous polymer selected from the group consisting of an aqueous linear urethanic polymer and an aqueous linear acrylic polymer. EP 0763378 A (TOYO INK) discloses similar pigment dispersing agents for non-aqueous pigment dispersions.

U.S. Pat. No. 5,420,187 (TOYO INK) discloses a pigment-dispersing agent obtained by polymerizing an addition-polymerizable monomer having an acidic functional group and another addition-polymerizable monomer in the presence of a polymerization initiator, the polymerization initiator being a diazotization product prepared by diazotizing at least one compound selected from the group consisting of an anthraquinone derivative having an aromatic amino group, an acridone derivative having an aromatic amino group, and an organic dyestuff having an aromatic amino group. In this pigment-dispersing agent, the colorant is located in the polymeric backbone itself.

U.S. 2003/0044707 (TOYO INK) discloses a dispersing agent for a pigment, including a specific compound having a structure wherein a phthalocyanine type molecular skeleton which is adsorptive on the pigment and an oligomer unit or polymer unit which prevents re-agglomeration of the pigment to bring out the effect of dispersion are covalently bonded, and having affinity for a medium or a solvent.

Current practice is that the exact or almost the exact chemical structure of the color pigment is incorporated as the anchor group in the polymeric dispersing agent to assure maximum affinity with the color pigment. As a consequence, each pigment has its own tailor-made polymeric dispersant. In practice, this requires the holding of an inventory of different polymeric dispersants for producing a complete range of color inkjet ink sets. The cyan ink with copper phthalocyanine as the pigment is a rare exception in that all desired properties are combined in the same pigment. But yellow pigments have to be selected based on the properties that are the most important in their application of inkjet ink. For example, some yellow pigments are selected for their light stability, while others are selected to obtain images having high color strength. The holding of such an inventory of different types of polymeric dispersants incurs financial penalties due to additional storage and logistical requirements as well as increasing the possibility of using the "wrong" polymeric dispersant for the production of a particular inkjet ink.

However the synthesis of such polymeric dispersants is complicated since the low solubility of the pigment induces low solubility of the monomer containing the pigment structure.

For consistent image quality, the inkjet ink requires a dispersion stability capable of dealing with high temperatures (above 60° C.) during transport of the ink to a customer and changes in the dispersion medium of the inkjet ink during use, for example, evaporation of solvent and increasing concentrations of humectants, penetrants, and other additives.

Therefore, it is highly desirable to be able to manufacture a range of stable pigmented inkjet inks using a single polymeric dispersant obtained by simple synthesis.

SUMMARY OF THE INVENTION

In order to overcome the problems described above, preferred embodiments of the present invention provide a monomer for preparing a polymeric dispersant obtainable by uncomplicated synthesis and suitable for different color pigments.

Further preferred embodiments of the present invention provide inkjet inks with high dispersion stability.

Further preferred embodiments of the present invention provide inkjet inks producing images of high image quality with a high optical density.

Further preferred embodiments of the invention will become apparent from the description hereinafter.

It has been surprisingly discovered that inkjet inks with high optical density and high stability can be obtained using a colored polymeric dispersant wherein a pending chromophore group exhibits a structural similarity with the color pigment, but is smaller in size than the color pigment.

A further preferred embodiment of the present invention has been achieved with a monomer with a chromophore group represented by Formula (I):

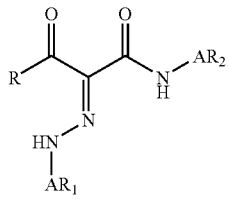

Formula (I)

wherein $AR_1$ represents a substituted or unsubstituted aromatic group;

$AR_2$ represents a substituted or unsubstituted aromatic group or a substituted or unsubstituted alkyl group;

and R represents a substituted or unsubstituted alkyl group, with the proviso that one of R, $AR_1$, and $AR_2$ has a substituent with a polymerizable functional group.

Other features, elements, processes, steps, characteristics and advantages of the present invention will become more apparent from the following detailed description of preferred embodiments of the present invention.

DETAILED DESCRIPTION OF PREFERRED EMBODIMENTS

Definitions

The term "colorant", as used in the preferred embodiments of the present invention, means dyes and pigments.

The term "dye", as used in the preferred embodiments of the present invention, means a colorant having a solubility of 10 mg/L or more in the medium in which it is applied and under the ambient conditions pertaining thereto.

The term "pigment" is defined in DIN 55943, herein incorporated by reference, as a coloring agent that is practically insoluble in the application medium under the pertaining ambient conditions, hence having a solubility of less than 10 mg/L therein.

The term "chromophore group", as used in the preferred embodiments of the present invention, means a group with an absorption maximum between 300 nm and 2,000 nm.

The term "pending chromophore group", as used in the preferred embodiments of the present invention, means a chromophore group occurring as a side group on the polymeric backbone and not a group in the polymeric backbone itself or occurring solely as an end group of the polymeric backbone.

The term "C.I." is used in the preferred embodiments of the present application as an abbreviation for Color Index.

The term "actinic radiation" as used in the preferred embodiments of the present invention, means electromagnetic radiation capable of initiating photochemical reactions.

The term "DP" is used in the preferred embodiments of the present application as an abbreviation for degree of polymerization, i.e., the number of structural units (monomers) in the average polymer molecule.

The term "PD" is used in the preferred embodiments of the present application as an abbreviation for polydispersity of a polymer.

The term "dispersion", as used in the preferred embodiments of the present invention, means an intimate mixture of at least two substances, one of which, called the dispersed phase or colloid, is uniformly distributed in a finely divided state through the second substance, called the dispersion medium.

The term "polymeric dispersant", as used in the preferred embodiments of the present invention, means a substance for promoting the formation and stabilization of a dispersion of one substance in a dispersion medium.

The term "copolymer", as used in the preferred embodiments of the present invention means a macromolecule in which two or more different species of monomer are incorporated into a polymer chain.

The term "block copolymer", as used in the preferred embodiments of the present invention, means a copolymer in which the monomers occur in relatively long alternate sequences in a chain.

The term "spectral separation factor" as used in the preferred embodiments of the present invention means the value obtained by calculating the ratio of the maximum absorbance $A_{max}$ (measured at wavelength $\lambda_{max}$) over the reference absorbance $A_{ref}$ determined at a higher wavelength $\lambda_{ref}$.

The abbreviation "SSF" is used in the preferred embodiments of the present invention for spectral separation factor.

The term "alkyl" means all variants possible for each number of carbon atoms in the alkyl group, i.e., for three carbon atoms: n-propyl and isopropyl; for four carbon atoms: n-butyl, isobutyl, and tertiary-butyl; for five carbon atoms: n-pentyl, 1,1-dimethyl-propyl, 2,2-dimethylpropyl, and 2-methylbutyl etc.

The term "acyl group" means —(C=O)-aryl and —(C=O)-alkyl groups.

The term "aliphatic group" means saturated straight chain, branched chain, and alicyclic hydrocarbon groups.

The term "unsaturated aliphatic group" means straight chain, branched chain, and alicyclic hydrocarbon groups which contain at least one double or triple bond.

The term "aromatic group" as used in the preferred embodiments of the present invention means an assemblage of cyclic conjugated carbon atoms, which are characterized by large resonance energies, e.g., benzene, naphthalene, and anthracene.

The term "alicyclic hydrocarbon group" means an assemblage of cyclic carbon atoms, which do not form an aromatic group, e.g., cyclohexane.

The term "heteroaromatic group" means an aromatic group wherein at least one of the cyclic conjugated carbon atoms is replaced by a non-carbon atom such as a nitrogen atom, a sulphur atom, a phosphorous atom, a selenium atom, and a tellurium atom.

The term "heterocyclic group" means an alicyclic hydrocarbon group wherein at least one of the cyclic carbon atoms is replaced by a non-carbon atom such as an oxygen atom, a nitrogen atom, a phosphorous atom, a silicon atom, a sulphur atom, a selenium atom, or a tellurium atom.

Monomers with a Chromophore Group

The monomer with a chromophore group according to a preferred embodiment of the present invention can be represented by Formula (I):

Formula (I)
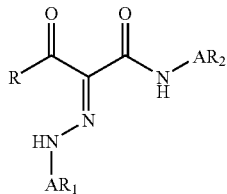

wherein, $AR_1$ represents a substituted or unsubstituted aromatic group;

$AR_2$ represents a substituted or unsubstituted aromatic group or a substituted or unsubstituted alkyl group;

and R represents a substituted or unsubstituted alkyl group, with the proviso that one of R, $AR_1$, and $AR_2$ has a substituent with a polymerizable functional group.

The monomer with a chromophore group according to a preferred embodiment of the present invention is preferably polymerizable by radical or cationic polymerization, most preferably by radical polymerization. The polymerizable functional group of the substituent with a polymerizable functional group on at least one of R, $AR_1$, and $AR_2$ is preferably an ethylenically unsaturated polymerizable functional group.

In a preferred embodiment, $AR_2$ of Formula (I) is replaced by an alkyl group, preferably methyl or ethyl.

In another preferred embodiment, $AR_2$ of Formula (I) is replaced by an aliphatic substituent with a polymerizable functional group, preferably an ethylenically unsaturated polymerizable functional group. Preferably, this aliphatic ethylenically unsaturated polymerizable functional group is represented by:

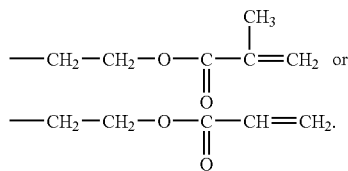

In a preferred embodiment, the monomer is represented by Formula (II):

Formula (II)
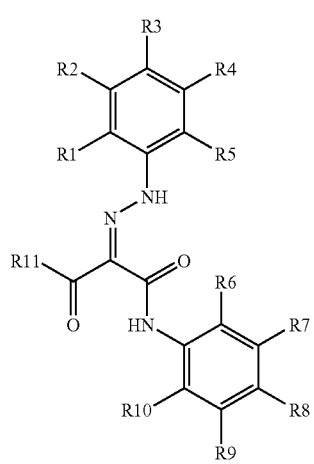

wherein one of R1 to R11 is the substituent with a polymerizable functional group;

R1 to R6, R9, and R10, if not representing the substituent with a polymerizable functional group, are independently selected from the group consisting of hydrogen, an alkyl group, an alkenyl group, an alkoxy group, an alcohol group, a carboxylic acid group, an ester group, an acyl group, a nitro group, and a halogen;

R7 and R8, if not representing the substituent with a polymerizable functional group and not independently selected from the group consisting of hydrogen, an alkyl group, an alkenyl group, an alkoxy group, an alcohol group, a carboxylic acid group, an ester group, an acyl group, a nitro group, and a halogen; together form a heterocyclic ring. In a preferred embodiment, the heterocyclic ring formed by R7 and R8 is imidazolone.

The polymerizable functional group is preferably an ethylenically unsaturated polymerizable functional group. The ethylenically unsaturated polymerizable functional group is preferably selected from the group consisting of a styrene, an acrylate, a methacrylate, an acrylamide, a methacrylamide, a maleimide, a vinyl ester, and a vinyl ether.

Suitable monomers according to Formula (I) include the monomers disclosed in Table 1: styrene derivatives, in Table 2: (meth)acrylate and (meth)acrylamide derivatives, and in Table 3: other polymerizable derivatives.

TABLE 1

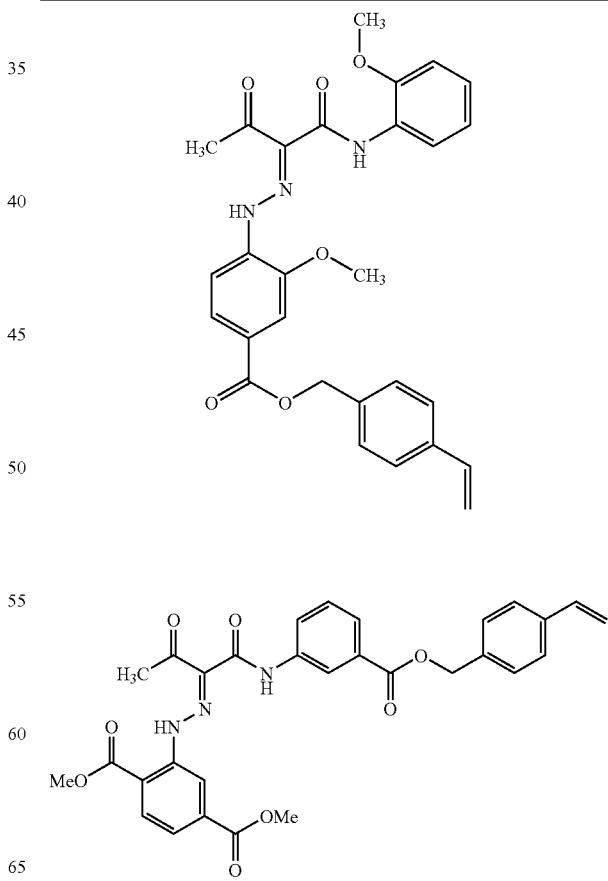

TABLE 1-continued
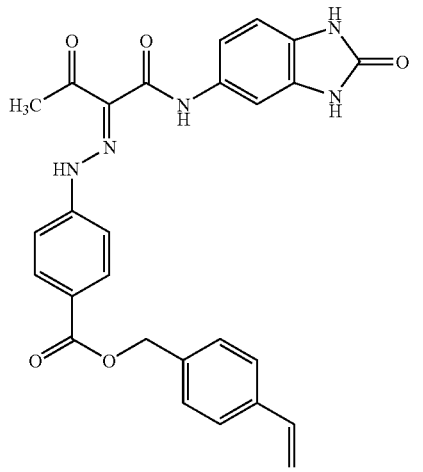
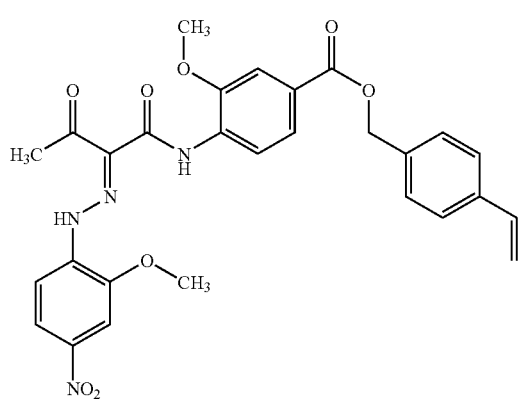
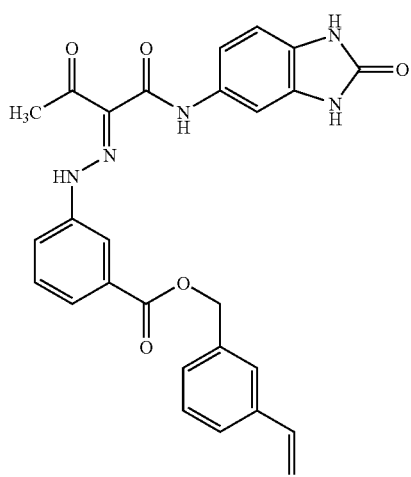
TABLE 1-continued
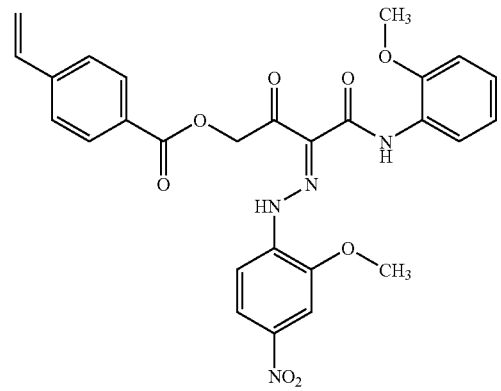
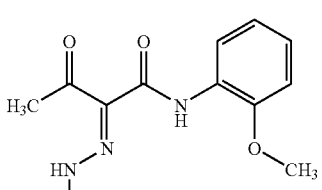
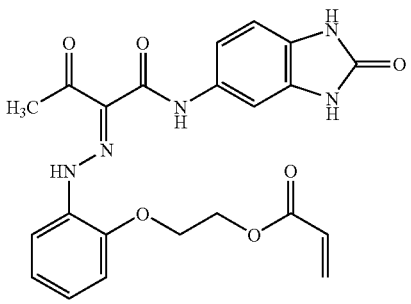
TABLE 2
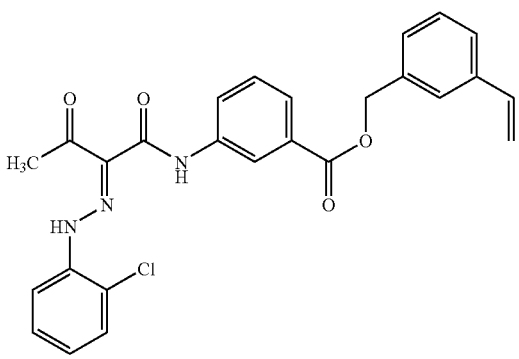
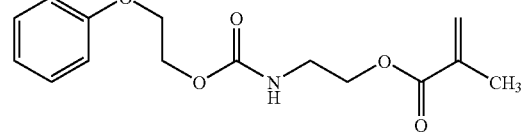

TABLE 2-continued
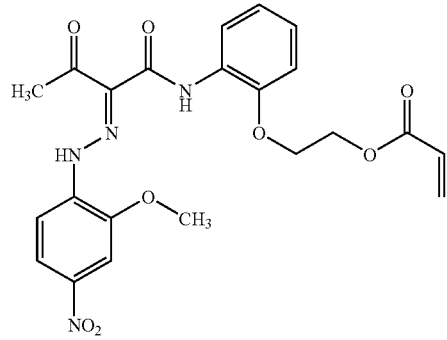
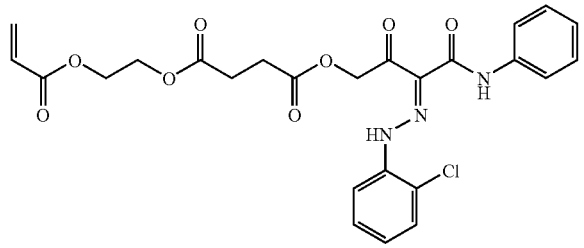
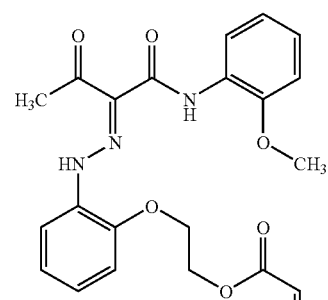
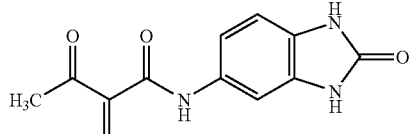
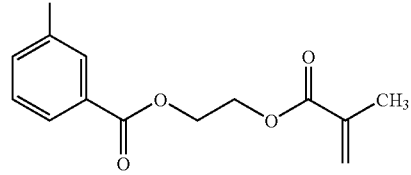
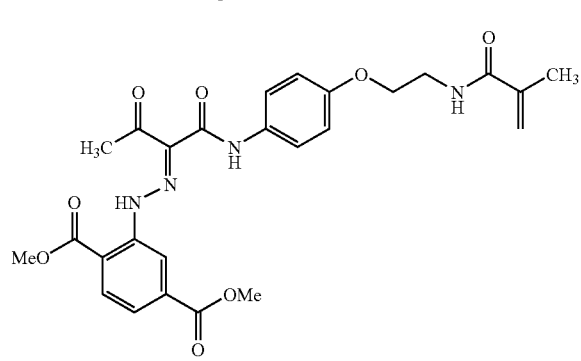
TABLE 2-continued
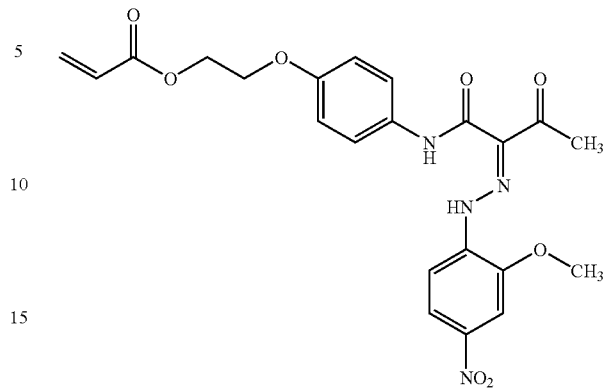
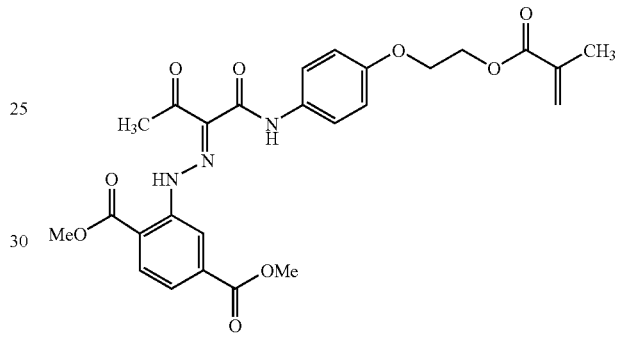
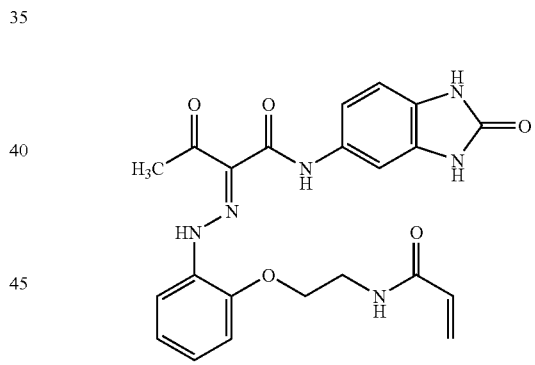
TABLE 3
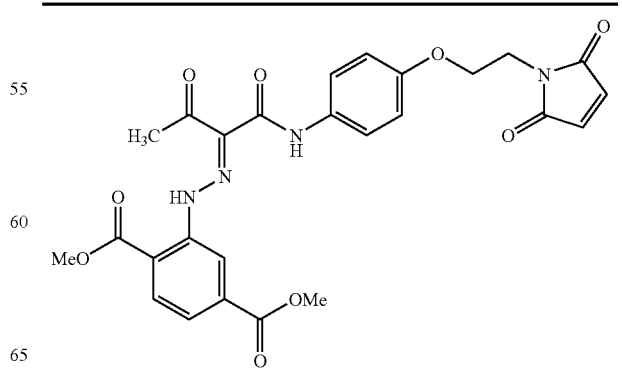

TABLE 3-continued

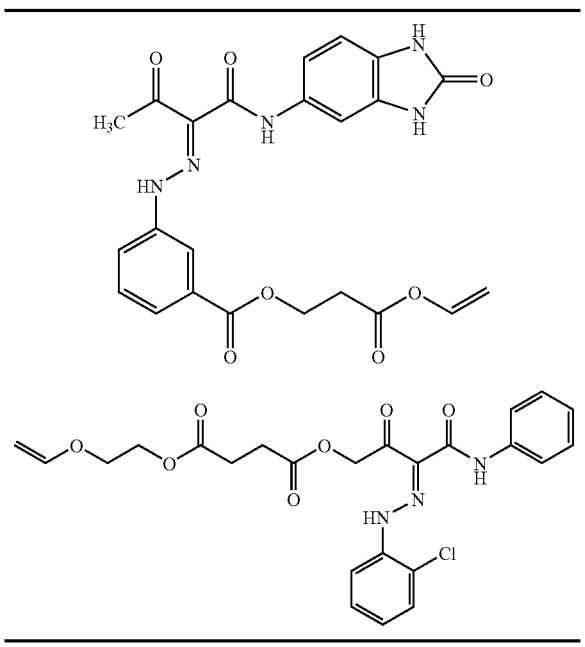

Pigmented Inkjet Ink

The pigmented inkjet ink contains at least three components: (i) a color pigment, (ii) a polymeric dispersant, and (iii) a dispersion medium.

The pigmented inkjet ink may further contain at least one surfactant.

The pigmented inkjet ink may further contain at least one biocide.

The pigmented inkjet ink may further contain at least one humectant and/or penetrant.

The pigmented inkjet ink may further contain at least one pH adjuster.

The pigmented inkjet ink may contain at least one humectant to prevent the clogging of the nozzle, due to its ability to slow down the evaporation rate of ink.

The viscosity of the pigmented inkjet ink is preferably lower than 100 mPa·s, more preferably lower than 30 mPa·s, and most preferably lower than 15 mPa·s at a shear rate of 100 $s^{-1}$ and a temperature between 20° C. and 110° C.

The pigmented inkjet ink according to a preferred embodiment of the present invention is preferably an aqueous solvent based or an oil based pigmented inkjet ink.

The pigmented inkjet ink may be curable and may contain monomers, oligomers, and/or prepolymers possessing different degrees of functionality. A mixture including combinations of mono-, di-, tri- and/or higher functionality monomers, oligomers, or prepolymers may be used. The initiator typically initiates the polymerization reaction. A catalyst called an initiator for initiating the polymerization reaction may be included in the curable pigmented inkjet ink. The initiator can be a thermal initiator, but is preferably a photo-initiator. The photo-initiator requires less energy to activate than the monomers, oligomers, and/or prepolymers to form the polymer. The photo-initiator suitable for use in the curable fluid may be a Norrish type I initiator, a Norrish type II initiator, or a photo-acid generator.

Color Pigments

The color pigment exhibits a structural similarity with the chromophore group in the monomer according to a preferred embodiment of the present invention but is preferably smaller in size. The chromophore group preferably has a molecular weight which is smaller than 95%, preferably smaller than 90%, preferably smaller than 85%, more preferably smaller than 75%, and most preferably smaller than 65% of the molecular weight of the color pigment.

The color pigment may be chosen from those disclosed by HERBST et al., Industrial Organic Pigments, Production, Properties, Applications; 3rd Edition, Wiley-VCH, 2004, ISBN 3527305769.

Particular preferred pigments are C.I. Pigment Yellow 12, 13, 14, 17, 55, 63, 81, 83, 87, 113, 121, 124, 152, 170, 171, 172, 174, and 188.

Particular preferred pigments are C.I. C. I. Pigment Yellow 1, 2, 3, 5, 6, 49, 65, 73, 74, 75, 97, 98, 111, 116, 130, and 213.

Particular preferred pigments are C.I. Pigment Yellow 120, 151, 154, 175, 180, 181, and 194.

Particular preferred pigments are C.I. Pigment Orange 1, 36, 60, 62, and 72.

The pigment particles in the pigmented inkjet ink should be sufficiently small to permit free flow of the ink through the inkjet printing device, especially at the ejecting nozzles. It is also desirable to use small particles for maximum color strength and to slow down sedimentation.

The average particle size of the pigment in the pigmented inkjet ink should be between 0.005 μm and 15 μm. Preferably, the average pigment particle size is between 0.005 μm and 5 μm, more preferably between 0.005 μm and 1 μm, particularly preferably between 0.005 μm and 0.3 μm, and most preferably between 0.040 μm and 0.150 μm. Larger pigment particle sizes may be used as long as the advantages of the present invention are achieved.

The pigment is preferably used in the pigmented inkjet ink in an amount of 0.1 wt % to 20 wt %, preferably 1 wt % to 10 wt % based on the total weight of the pigmented inkjet ink.

Polymeric Dispersants

The polymeric dispersant for the pigmented inkjet ink has a polymeric backbone including one or more monomers according to a preferred embodiment of the present invention. The other monomer species constituting the polymeric backbone of the polymeric dispersant are required for the compatibility between polymeric dispersant and dispersion medium. It is not required that the rest of the polymeric backbone has an affinity for the pigment. For example, the rest of the polymeric backbone of a dispersant for aqueous inkjet inks can be a homopolymer of acrylic acid monomers. A homopolymer is generally incapable of dispersing pigments, but the presence of one or more monomeric units with a chromophore group exhibiting a similarity with the pigment ensures an adequate affinity between polymeric dispersant and pigment surface.

The polymeric backbone can also be a statistical copolymer, a block copolymer, a graft copolymer, a comb polymer, or an alternating copolymer. Also suitable as polymeric backbone is a gradient copolymer as disclosed by MATYJASZEWSKI et al., Atom Transfer Radical Polymerization, Chem. Reviews 2001, Vol. 101, pp. 2921-2990. Sometimes it can be useful to include a number of monomers with a high affinity for the pigment surface to enhance certain properties of the inks, e.g., dispersion stability. For example, the polymeric backbone of a dispersant for aqueous inkjet inks may contain hydrophobic monomers to increase the affinity of the polymeric dispersant for the pigment surface. However in enhancing this affinity for the pigment surface, care should be taken that enough of the polymeric backbone sticks out to make the pigment particles compatible with the dispersion medium.

Preferably, at most 45%, preferably at most 30% of the monomer units of the polymeric backbone of the polymeric dispersant used in the pigmented inkjet ink according to a preferred embodiment of the present invention have a chromophore group.

In graft copolymers, the use of grafted chains of methoxypolyethyleneglycol (MPEG) has been found to be very advantageous in aqueous inkjet inks. For solvent-based inkjet inks the use of grafted chains of polyester were found to be very advantageous. A preferred MPEG macromonomer is BISOMER™ MPEG 350MA (methoxypolyethyleneglycol methacrylate) from LAPORTE INDUSTRIES LTD.

Preferred grafted chains of polyester in non-aqueous inkjet inks are derived from δ-valerolactone, ε-caprolactone, and/or $C_1$ to $C_4$ alkyl substituted ε-caprolactone. The grafted chains can be introduced into the polymeric dispersant through CDI coupling of a polyester-OH chain with a carboxylic acid group of, for example, an acrylic acid monomer in the polymeric backbone of the dispersant. However, it was observed that grafting by free radical polymerization, wherein the polyester chain already coupled to the carboxylic acid group of an acrylic acid monomer was used as a macro-monomer, not only resulted in better dispersion quality and stability of the inkjet inks but also obtained a more reproducible polymeric dispersant synthesis requiring less purification.

For radiation curable inks with the dispersion medium including or consisting of monomers and/or oligomers, many (co)polymers having good solubility in the dispersion medium are suitable for the polymer backbone of the polymeric dispersant.

The polymeric backbone consists preferably of no more than 2 or 3 monomer species. These monomer species can be any monomer and/or oligomer found in the Polymer Handbook, Vol. 1+2, 4th Edition, edited by J. BRANDRUP et al., Wiley-Interscience, 1999.

Suitable examples of monomers include: acrylic acid, methacrylic acid, maleic acid, acryloyloxybenzoic acid and methacryloyloxybenzoic acid (or their salts), and maleic anhydride; alkyl(meth)acrylates (linear, branched, and cycloalkyl) such as methyl(meth)acrylate, n-butyl(meth)acrylate, tert-butyl(meth)acrylate, cyclohexyl(meth)acrylate and 2-ethylhexyl(meth)acrylate; aryl(meth)acrylates such as benzyl(meth)acrylate and phenyl(meth)acrylate; hydroxyalkyl(meth)acrylates such as hydroxyethyl(meth)acrylate and hydroxypropyl(meth)acrylate; (meth)acrylates with other types of functionalities (e.g., oxirane, amino, fluoro, polyethylene oxide, phosphate-substituted) such as glycidyl (meth)acrylate, dimethylaminoethyl(meth)acrylate, trifluoroethyl acrylate, methoxypolyethyleneglycol(meth)acrylate and tripropyleneglycol(meth)acrylate phosphate; allyl derivatives such as allyl glycidyl ether; styrenics such as styrene, 4-methylstyrene, 4-hydroxystyrene, and 4-acetoxystyrene; (meth)acrylonitrile; (meth)acrylamides (including N-mono and N,N-disubstituted) such as N-benzyl(meth)acrylamide; maleimides such as N-phenyl maleimide, N-benzyl maleimide, and N-ethyl maleimide; vinyl derivatives such as vinylcaprolactam, vinylpyrrolidone, vinylimidazole, vinylnaphthalene, and vinyl halides; vinylethers such as vinylmethyl ether; and vinylesters of carboxylic acids such as vinylacetate and vinylbutyrate.

The polymeric dispersant used in the pigmented inkjet ink preferably has a polymeric backbone with a polymerization degree DP between 5 and 1,000, more preferably between 10 and 500, and most preferably between 10 and 100.

The polymeric dispersant used in the pigmented inkjet ink preferably has a number average molecular weight Mn between 500 and 30,000, more preferably between 1,500 and 10,000.

The polymeric dispersant has preferably a polymeric dispersity PD smaller than 2, more preferably smaller than 1.75, and most preferably smaller than 1.5.

The polymeric dispersant is preferably used in the pigmented inkjet ink in an amount of 5 wt % to 600 wt %, more preferably 10 wt % to 100 wt % based on the weight of the pigment.

Synthesis

The polymeric dispersant used in the pigmented inkjet ink is preferably prepared by copolymerization with the monomer according to a preferred embodiment of the present invention.

The polymerization process may be a condensation polymerization, in which the chain growth is accompanied by elimination of small molecules such as water or methanol or an addition polymerization, in which the polymer is formed without the loss of other materials. Polymerization of the monomers can be conducted according to any conventional method such as bulk polymerization and semi-continuous polymerization.

The synthesis is preferably performed by a controlled radical polymerization (CRP) technique. Suitable polymerization techniques include ATRP (atom transfer radical polymerization), RAFT (reversible addition-fragmentation chain transfer polymerization), MADIX (reversible addition-fragmentation chain transfer process, using a transfer active xanthate), catalytic chain transfer (e.g., using cobalt complexes), GTP (group transfer polymerization), or nitroxide (e.g., TEMPO) mediated polymerizations.

Polymeric dispersants prepared by copolymerizing monomers of the polymeric backbone and monomers containing a chromophore group were found to have superior properties compared to polymeric dispersants prepared by modification of a (co)polymer with a chromophore having a reactive group. The polymerization method using monomers containing a chromophore group offers the advantage of well-controlled design of polymeric dispersants for a wide variety of dispersion media. Due to its low solubility, a monomer containing the complete color pigment as a chromophore group poses problems both in the synthesis of the polymeric dispersants, as well as the suitability of the polymeric dispersant for a wide variety of dispersion media and pigments.

Dispersion Media

The dispersion medium used in the pigmented inkjet ink is a liquid. The dispersion medium may consist of water and/or organic solvent(s).

If the pigmented inkjet ink is a curable pigmented inkjet ink, water and/or organic solvent(s) are replaced by one or more monomers and/or oligomers to obtain a liquid dispersion medium. Sometimes, it can be advantageous to add a small amount of an organic solvent to improve the dissolution of the dispersant. The content of organic solvent should be lower than 20 wt % based on the total weight of the pigmented inkjet ink.

Suitable organic solvents include alcohols, aromatic hydrocarbons, ketones, esters, aliphatic hydrocarbons, higher fatty acids, carbitols, cellosolves, and higher fatty acid esters. Suitable alcohols include, methanol, ethanol, propanol and 1-butanol, 1-pentanol, 2-butanol, and t.-butanol. Suitable aromatic hydrocarbons include toluene and xylene. Suitable ketones include methyl ethyl ketone, methyl isobutyl ketone, 2,4-pentanedione, and hexafluoroacetone. Also, glycol, glycolethers, N-methylpyrrolidone, N,N-dimethylacetamid, and N,N-dimethylformamid may be used.

Suitable monomers and oligomers can be found in Polymer Handbook, Vol. 1+2, 4th Edition, edited by J. BRANDRUP et al., Wiley-Interscience, 1999.

Suitable examples of monomers for curable pigmented inkjet inks include: acrylic acid, methacrylic acid, maleic acid (or their salts), and maleic anhydride; alkyl(meth)acrylates (linear, branched, and cycloalkyl) such as methyl(meth)acrylate, n-butyl(meth)acrylate, tert-butyl(meth)acrylate, cyclohexyl(meth)acrylate, and 2-ethylhexyl(meth)acrylate; aryl (meth)acrylates such as benzyl(meth)acrylate and phenyl (meth)acrylate; hydroxyalkyl(meth)acrylates such as hydroxyethyl(meth)acrylate and hydroxypropyl(meth)acrylate; (meth)acrylates with other types of functionalities (e.g., oxirane, amino, fluoro, polyethylene oxide, phosphate-substituted) such as glycidyl(meth)acrylate, dimethylaminoethyl (meth)acrylate, trifluoroethyl acrylate, methoxypolyethyleneglycol(meth)acrylate and tripropyleneglycol(meth) acrylate phosphate; allyl derivatives such as allyl glycidyl ether; styrenics such as styrene, 4-methylstyrene, 4-hydroxystyrene, and 4-acetoxystyrene; (meth)acrylonitrile; (meth) acrylamides (including N-mono and N,N-disubstituted) such as N-benzyl(meth)acrylamide; maleimides such as N-phenyl maleimide, N-benzyl maleimide, and N-ethyl maleimide; vinyl derivatives such as vinylcaprolactam, vinylpyrrolidone, vinylimidazole, vinylnaphthalene, and vinyl halides; vinylethers such as vinylmethyl ether; and vinylesters of carboxylic acids such as vinylacetate and vinylbutyrate.

A combination of monomers, oligomers, and/or prepolymers may also be used. The monomers, oligomers, and/or prepolymers may possess different degrees of functionality, and a mixture including combinations of mono-, di-, tri- and higher functionality monomers, oligomers, and/or prepolymers may be used.

In another preferred embodiment, the monomer is part of the dispersion medium.

For oil based inkjet inks, the dispersion medium can be any suitable oil including aromatic oils, paraffinic oils, extracted paraffinic oils, naphthenic oils, extracted napthenic oils, hydrotreated light or heavy oils, vegetable oils and derivatives and mixtures thereof. Paraffinic oils can be normal paraffin types (octane and higher alkanes), isoparaffins (isooctane and higher iso-alkanes) and cycloparaffins (cyclooctane and higher cyclo-alkanes), and mixtures of paraffin oils.

Surfactants

The pigmented inkjet ink may contain at least one surfactant. The surfactant(s) can be anionic, cationic, non-ionic, or zwitter-ionic and are usually added in a total quantity less than 20 wt % based on the total weight of the pigmented inkjet ink and particularly in a total less than 10 wt % based on the total weight of the pigmented inkjet ink.

Suitable surfactants for the pigmented inkjet ink include fatty acid salts, ester salts of a higher alcohol, alkylbenzene sulphonate salts, sulphosuccinate ester salts and phosphate ester salts of a higher alcohol (for example, sodium dodecylbenzenesulphonate and sodium dioctylsulphosuccinate), ethylene oxide adducts of a higher alcohol, ethylene oxide adducts of an alkylphenol, ethylene oxide adducts of a polyhydric alcohol fatty acid ester, and acetylene glycol and ethylene oxide adducts thereof (for example, polyoxyethylene nonylphenyl ether, and SURFYNOL™ 104, 104H, 440, 465, and TG available from AIR PRODUCTS & CHEMICALS INC.).

Biocides

Suitable biocides for the pigmented inkjet ink include sodium dehydroacetate, 2-phenoxyethanol, sodium benzoate, sodium pyridinethion-1-oxide, ethyl p-hydroxybenzoate, and 1,2-benzisothiazolin-3-one and salts thereof.

Preferred biocides are Bronidox™ available from HENKEL and Proxel™ GXL available from AVECIA.

A biocide is preferably added in an amount of 0.001 wt % to 3 wt %, more preferably 0.01 wt % to 1.00 wt %, each based on the total weight of the pigmented inkjet ink.

pH Adjusters

The pigmented inkjet ink may contain at least one pH adjuster. Suitable pH adjusters include NaOH, KOH, NEt$_3$, NH$_3$, HCl, HNO$_3$, H$_2$SO$_4$, and (poly)alkanolamines such as triethanolamine and 2-amino-2-methyl-1-propanol. Preferred pH adjusters are NaOH and H$_2$SO$_4$.

Humectants/Penetrants

Suitable humectants include triacetin, N-methyl-2-pyrrolidone, glycerol, urea, thiourea, ethylene urea, alkyl urea, alkyl thiourea, dialkyl urea and dialkyl thiourea, diols, including ethanediols, propanediols, propanetriols, butanediols, pentanediols, and hexanediols; glycols, including propylene glycol, polypropylene glycol, ethylene glycol, polyethylene glycol, diethylene glycol, tetraethylene glycol, and mixtures and derivatives thereof. Preferred humectants are triethylene glycol mono butylether, glycerol and 1,2-hexanediol. The humectant is preferably added to the inkjet ink formulation in an amount of 0.1 wt % to 40 wt % of the formulation, more preferably 0.1 wt % to 10 wt % of the formulation, and most preferably approximately 4.0 wt % to 6.0 wt %.

Preparation of Pigmented Inkjet Inks

The pigmented inkjet ink may be prepared by precipitating or milling the pigment in the dispersion medium in the presence of the polymeric dispersant.

Mixing apparatuses may include a pressure kneader, an open kneader, a planetary mixer, a dissolver, and a Dalton Universal Mixer. Suitable milling and dispersion apparatuses are a ball mill, a pearl mill, a colloid mill, a high-speed disperser, double rollers, a bead mill, a paint conditioner, and triple rollers. The dispersions may also be prepared using ultrasonic energy.

Many different types of materials may be used as milling media, such as glasses, ceramics, metals, and plastics. In a preferred embodiment, the grinding media can include particles, preferably substantially spherical in shape, e.g., beads consisting essentially of a polymeric resin or yttrium stabilized zirconium beads.

In the process of mixing, milling, and dispersion, each process is performed with cooling to prevent build up of heat, and for radiation curable inkjet inks as much as possible under light conditions in which actinic radiation has been substantially excluded.

The inkjet ink may contain more than one pigment, the inkjet ink may be prepared using separate dispersions for each pigment, or alternatively several pigments may be mixed and co-milled in preparing the dispersion.

The dispersion process can be carried out in a continuous, batch, or semi-batch mode.

The preferred amounts and ratios of the ingredients of the mill grind will vary widely depending upon the specific materials and the intended applications. The contents of the milling mixture include the mill grind and the milling media. The mill grind includes pigment, polymeric dispersant, and a liquid carrier such as water. For inkjet inks, the pigment is usually present in the mill grind at 1 wt % to 50 wt %, excluding the milling media. The weight ratio of pigment over polymeric dispersant is preferably 20:1 to 1:2.

The milling time can vary widely and depends upon the pigment, mechanical means and residence conditions selected, the initial and desired final particle size, etc. In a preferred embodiment of the present invention, pigment dispersions with an average particle size of less than 100 nm may be prepared.

After milling is completed, the milling media is separated from the milled particulate product (in either a dry or liquid dispersion form) using conventional separation techniques, such as by filtration, sieving through a mesh screen, and the like. Often the sieve is built into the mill, e.g., for a bead mill. The milled pigment concentrate is preferably separated from the milling media by filtration.

In general, it is desirable to make the inkjet inks in the form of a concentrated mill grind, which is subsequently diluted to the appropriate concentration for use in the inkjet printing system. This technique permits preparation of a greater quantity of pigmented ink from the equipment. By dilution, the inkjet ink is adjusted to the desired viscosity, surface tension, color, hue, saturation density, and print area coverage for the particular application.

Spectral Separation Factor

The spectral separation factor SSF was found to be an excellent measure to characterize a pigmented inkjet ink, as it takes into account properties related to light-absorption (e.g., wavelength of maximum absorbance $\lambda_{max}$, shape of the absorption spectrum and absorbance-value at $\lambda_{max}$) as well as properties related to the dispersion quality and stability.

A measurement of the absorbance at a higher wavelength gives an indication on the shape of the absorption spectrum. The dispersion quality can be evaluated based on the phenomenon of light scattering induced by solid particles in solutions. When measured in transmission, light scattering in pigment inks may be detected as an increased absorbance at higher wavelengths than the absorption peak of the actual pigment. The dispersion stability can be evaluated by comparing the SSF before and after a heat treatment of, e.g., a week at 80° C.

The spectral separation factor SSF of the ink is calculated by using the data of the recorded spectrum of an ink solution or a jetted image on a substrate and comparing the maximum absorbance to the absorbance at a higher reference wavelength $\lambda_{ref}$. The spectral separation factor is calculated as the ratio of the maximum absorbance $A_{max}$ over the absorbance $A_{ref}$ at a reference wavelength.

$$SSF = \frac{A_{max}}{A_{ref}}$$

The SSF is an excellent tool to design inkjet ink sets with a large color gamut. Often, inkjet ink sets are now commercialized, wherein the different inks are not sufficiently matched with each other. For example, the combined absorption of all inks does not give a complete absorption over the whole visible spectrum, e.g., "gaps" exist between the absorption spectra of the colorants. Another problem is that one ink might be absorbing in the range of another ink. The resulting color gamut of these inkjet ink sets is low or mediocre.

EXAMPLES

Materials

All materials used in the following examples were readily available from standard sources such as Aldrich Chemical Co. (Belgium) and Acros (Belgium) unless otherwise specified. The water used was deionized water.

SMA 1000P is a styrene maleic anhydride alternating copolymer available from ATOFINA.

VERSICOL E5 was obtained from ALLIED COLLOIDS MANUFACTURING CO LTD as a 25% wt solution of pAA in water. This solution was freeze-dried to afford the dry powder of polyacrylic acid that was subsequently used for modification reactions.

Raney Nickel™ is a catalysator from DEGUSSA.

WAKO V-601 is dimethyl 2,2'-azobisisobutyrate from Wako Pure Chemical Industries, Ltd.

MSTY or alpha methylstyrene dimer is 2,4-diphenyl-4-methyl-1-pentene from Goi Chemical Co., Ltd.

AA is acrylic acid from ACROS.

MAA is methacrylic acid from ACROS.

BA is butyl acrylate from ACROS.

EHA is 2-ethyl hexyl acrylate from ACROS.

STY is styrene from ACROS.

Proxel™ Ultra 5 from AVECIA.

Glycerol from ACROS.

1,2-propanediol from CALDIC CHEMIE NV.

Surfynol™ 104H from AIR PRODUCTS & CHEMICALS INC.

PY12 is the abbreviation for C.I. Pigment Yellow 12 for which Permanent™ Yellow DHG from CLARIANT was used.

PY13 is the abbreviation for C.I. Pigment Yellow 13 for which Irgalite™ Yellow BAW from CIBA was used PY14 is the abbreviation for C.I. Pigment Yellow 14 for which Sunbrite Yellow 14/274-2168 from SUN CHEMICAL was used PY17 is the abbreviation for C.I. Pigment Yellow 17 for which Graphtol™ Yellow GG from CLARIANT was used The chemical structure of the color pigments used is listed in Table 4.

TABLE 4

PY17

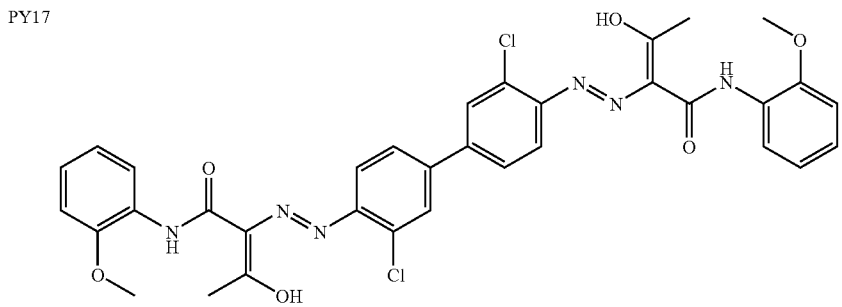

| | |
|---|---|
| PY74 | 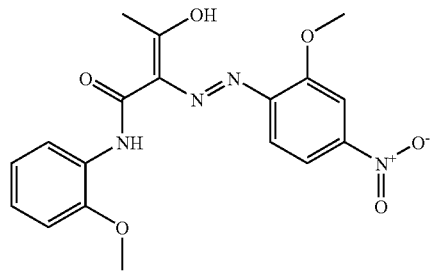 |

Measurement Methods

1. Measurement of SSF

The spectral separation factor SSF of the ink was calculating by using the data of the recorded spectrum of an ink solution and comparing the maximum absorbance to the absorbance at a reference wavelength. The choice of this reference wavelength is dependent on the pigment(s) used:

if the color ink has a maximum absorbance $A_{max}$ between 400 nm and 500 nm, then the absorbance $A_{ref}$ must be determined at a reference wavelength of 600 nm;

if the color ink has a maximum absorbance $A_{max}$ between 500 nm and 600 nm, then the absorbance $A_{ref}$ must be determined at a reference wavelength of 650 nm;

if the color ink has a maximum absorbance $A_{max}$ between 600 nm and 700 nm, then the absorbance $A_{ref}$ must be determined at a reference wavelength of 830 nm.

The absorbance was determined in transmission with a Shimadzu UV-2101 PC double beam-spectrophotometer. The ink was diluted to have a pigment concentration of 0.002%. In the case of a magenta ink, the ink was diluted to have a pigment concentration of 0.005%. A spectrophotometric measurement of the UV-VIS-NIR absorption spectrum of the diluted ink was performed in transmission-mode with a double beam-spectrophotometer using the settings of Table 5. Quartz cells with a path length of 10 mm were used and water was chosen as a blank.

TABLE 5

| Mode | Absorbance |
|---|---|
| Wavelength range | 240-900 nm |
| Slit width | 2.0 nm |
| Scan interval | 1.0 nm |
| Scan speed | Fast (1165 nm/min) |
| Detector | photo-multiplier(UV-VIS) |

Efficient pigmented inkjet inks exhibiting a narrow absorption spectrum and a high maximum absorbance have a value for SSF of at least 30.

2. Dispersion Stability

The dispersion stability was evaluated by comparing the SSF before and after a heat treatment of one week at 80° C. Pigmented inkjet inks exhibiting good dispersion stability have a SSF after heat treatment still larger than 30.

3. Polymer Analysis

Unless otherwise specified, all polymers have been characterized with gel permeation chromatography (GPC) and nuclear magnetic resonance spectroscopy (NMR) using the following methods. Random or block copolymers were analyzed with NMR by dissolving them in a deuterated solvent.

For $^1$H-NMR±20 mg polymer was dissolved in 0.8 mL CDCl$_3$ or DMSO-d6 or acetonitrile-d3 or D$_2$O (with or without NaOD addition). Spectra were recorded on a Varian Inova 400 MHz instrument equipped with an ID-probe. For $^{13}$C-NMR±200 mg polymer was dissolved in 0.8 mL CDCl$_3$ or DMSO-d6 or acetonitrile-d3 or D$_2$O (with or without NaOD addition). Spectra were recorded on a Varian Gemini2000 300 MHz equipped with a SW-probe.

Mn, Mw, and polydispersity (PD) values were determined using gel permeation chromatography. For polymers dissolvable in organic solvents PL-mixed B columns (Polymer Laboratories Ltd) were used with THF+5% acetic acid as mobile phase using polystyrene with known molecular weights as calibration standards. These polymers were dissolved in the mobile phase at a concentration of 1 mg/mL. For polymers dissolvable in water PL Aquagel OH-60, OH-50, OH-40, and/or OH-30 (Polymer Laboratories Ltd) column combinations were used depending on the molecular weight region of the polymers under investigation. As mobile phase water/methanol mixtures adjusted to pH 9.2 with, e.g., disodiumhydrogen phosphate were used with or without the addition of neutral salts, e.g., sodium nitrate. As calibration standards polyacrylic acids with known molecular weights were used. The polymers were dissolved in either water or water made basic with ammonium hydroxide at a concentration of 1 mg/mL. Refractive index detection was used.

An example is now given to illustrate the calculation of the average composition of a random (=statistical) copolymer P(MAA-c-EHA).

The Mn of the copolymer was determined with GPC to be 5000.

The molar percentage of each monomer type by NMR was determined to be: 45 mole % MAA and 55 mole % EHA.

Calculation:

$$(0.45 \times M_{MAA}) + (0.55 \times M_{EHA}) = 140.09$$

$$5000/140.09 = \text{total number of monomeric units in average polymer chain} = 36$$

$$\text{Average number of } MAA \text{ units} = 0.45 \times (5000/140.09) = 16 \text{ units}$$

$$\text{Average number of } EHA \text{ units} = 0.55 \times (5000/140.09) = 20 \text{ units}$$

Thus, the average composition is P(MAA$_{16}$-c-EHA$_{20}$).

4. Particle Size

The particle size of pigment particles in the pigmented inkjet ink was determined by photon correlation spectroscopy at a wavelength of 633 nm with a 4 mW HeNe laser on a diluted sample of the pigmented inkjet ink. The particle size analyzer used was a Malvern™ nano-S available from Goffin-Meyvis.

The sample was prepared by addition of one drop of ink to a cuvet containing 1.5 mL water and mixed until a homogenous sample was obtained. The measured particle size is the average value of 3 consecutive measurements consisting of 6 runs of 20 seconds. For good ink jet characteristics (jetting characteristics and print quality) the average particle size of the dispersed particles is preferably below 150 nm.

5. Calculation of % MW

The % MW is calculated as the ratio of the molecular weight of the chromophore group over the molecular weight of the color pigment multiplied by 100.

Example 1

This example illustrates that different pigments for inkjet inks can be dispersed using the same polymeric dispersant prepared with a monomer in accordance with a preferred embodiment of the present invention having a smaller chromophore group with a structural similarity to the pigment. The polymeric backbone of the dispersant is a homopolymer, which are known to have poor dispersing capability.

Polymeric Dispersants DISP-1 and DISP-2

A comparison was made with a homopolymer and a homopolymer modified with a chromophore.

VERSICOL E5, a homopolymer of acrylic acid was used as polymeric dispersant DISP-1. The polymeric dispersant DISP-2 was prepared by modifying VERSICOL E5 through esterification with the chromophore MC-2.

Chromophore MC-2

The formation of the chromophore MC-2 was accomplished by diazotation of compound MC-1D and subsequent coupling in the compound MC-2B.

Preparation of Compound MC-1C

The vessel used to carry out this reaction was a 3 necked flask equipped with a stirrer, a cooler, and a dropping-funnel. To a solution of 13.9 g (0.1 mol) 2-nitrophenol (compound MC-1A) in 100 mL dimethylformamide was added 31.8 g (0.3 mol) of sodiumcarbonate. The mixture was heated to a temperature of about 150° C.-160° C. and 16.1 g (0.2 mol) of 2-chloroethanol (compound MC-1B) was added drop-wise. After addition of the 2-chloroethanol, the temperature was maintained at a temperature between 150° C. and 160° C. for about 7 hours. The charge was cooled while stirring and the formed inorganic salts were filtered off. The filtrate was concentrated by evaporation at a temperature of 40° C. until a red colored mixture of oil and solid was formed. Then the oil was dissolved in methylenechloride and the inorganic salts were filtered off. The filtrate was evaporated for a second time and the formed yellow oil was purified by preparative column chromatography. The yield of compound MC-1C was 79%.

Synthesis Scheme of Compound MC-1C:

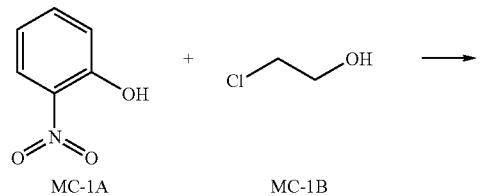

MC-1A    MC-1B

-continued

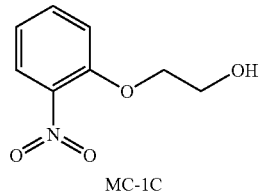

MC-1C

Preparation of Compound MC-1D

Compound MC-1D was made by catalytic reduction of compound MC-1C with hydrogen. A reactor was filled with 18.3 g (0.1 mol) of compound MC-1C in 100 mL ethanol and 1 mL of Raney Nickel™ slurry was added. The volume of the mixture was set to 150 mL with ethanol and the reduction was carried out at a starting temperature of 35° C. under an initial $H_2$-pressure of 60 bar. By shaking the reactor, the exothermic reaction started and the temperature increased to about 60° C. After reduction, the charge was mixed during 1 hour and the Raney Nickel™ was filtered off. The filtrate was evaporated at a temperature of 50° C. until the desired white crystalline product MC-1D appeared. The yield of compound MC-1D was 95%.

Synthesis Scheme of Compound MC-1D:

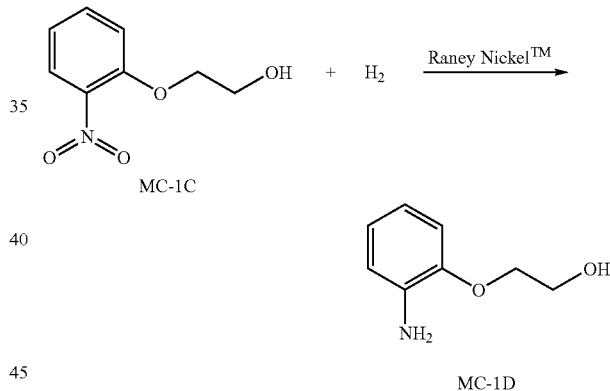

Preparation of Chromophore MC-2

29.98 mL (0.36 mol) of concentrated hydrochloric acid was added to a suspension of 15.3 g (0.1 mol) of compound MC-1D in 300 mL water. This mixture was cooled to a temperature of about 0-5° C. and 8.97 g (0.13 mol) of sodiumnitrite was added. The diazonium-salt was kept at a temperature between 0° C. and 5° C. After 15 minutes, the excess of nitrite was neutralized by adding 3.0 g (0.03 mol) of sulfamic acid and a pH of 7 was obtained by adding 25.2 g (0.3 mol) of sodiumcarbonate. While the diazionium-salt was made, 20.7 g (0.1 mol) of MC-2B from ACROS was dissolved in a mixture of 500 mL methanol and 10.0 mL (0.1 mol) 29% sodiumhydroxide-solution. This solution was added drop-wise into the diazonium-salt solution and a yellow suspension was immediately formed. The temperature was maintained between 0° C. and 5° C. for about 3 hours and the yellow product MC-2 was filtered and washed with methanol. The yield of the chromophore MC-2 was 92%.

Synthesis Scheme of the Chromophore MC-2:

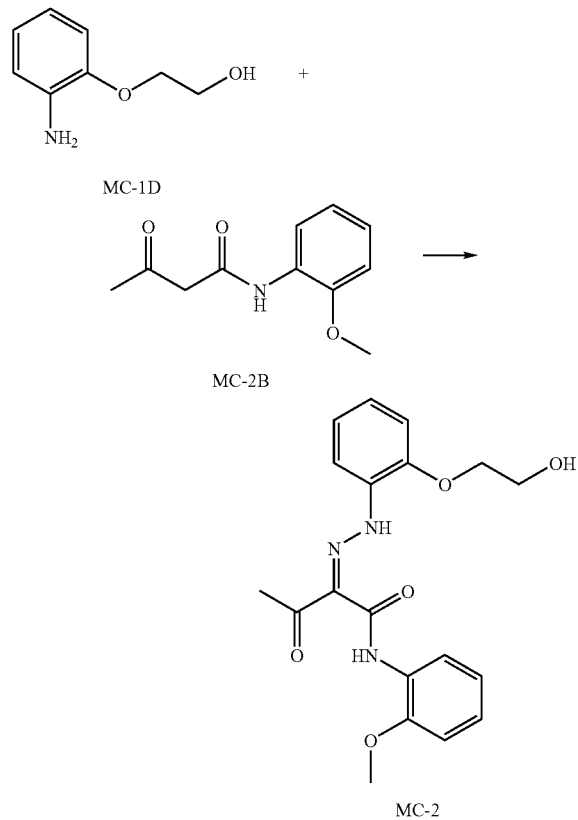

Synthesis of Polymeric Dispersant DISP-2

The polymeric dispersant DISP-2 was prepared by modifying DISP-1 (VERSICOL E5) with the chromophore MC-2. The resulting pending chromophore group PC-2 was linked by C* to the polymeric backbone through a linking group L containing an ester bond.

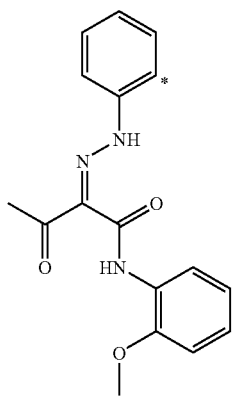

The reaction was performed in a three-necked round-bottomed flask that was equipped with a stirrer, a cooler, and a bubble-counter on top. 4 g of the polyacrylic acid homopolymer (VERSICOL E5 as powder form) was introduced in the flask and dissolved in 40 mL of anhydrous dimethylacetamide (DMA). A slight flux of nitrogen was circulated through the flask. After (VERSICOL E5) was dissolved, 4.48 g of 1,1'-carbonyldiimidazole (CDI) was added and $CO_2$ evolution was observed. The reaction was further stirred at room temperature for 1 hour after which 4.10 g of the chromophore MC-2 in combination with 169 mg of the catalyst dimethylaminopyridine (DMAP) were added. The heterogeneous mixture was stirred and heated to 80° C. for 20 hours. The reaction mixture was cooled to room temperature and was treated by slowly adding 10 mL of a 2% v/v of acetic acid/water solution.

The heterogeneous mixture obtained was basified to pH 10 with NaOH and filtrated to remove remaining precipitates. The solution was dialyzed in water (Regenerated Cellulose Dialysis Membrane of MWCO of 1,000 Dalton—SPECTRA/POR™ 6) for two days and precipitates that appeared were filtered off again. The obtained solution was freeze-dried to give a fluffy yellow powder. Yield of DISP-2 was 4.8 g.

Analytical results of DISP-2: GPC: Mn=1208; Mw=4960; PD=4.11

(aqueous GPC; calibrated vs. PAA-standards)

The degree of substitution was determined by $^1$H-NMR-spectroscopy and expressed as the percentage of AA monomeric units. The degree of substitution of DISP-2 with the chromophore MC-2 was 13 molar %.

Polymeric Dispersants DISP-3 to DISP-6

The polymeric dispersants DISP-7 to DISP-8 were prepared by copolymerizing a monomer MONC-1 already containing the same chromophore group PC-2.

Synthesis of the Monomer MONC-1

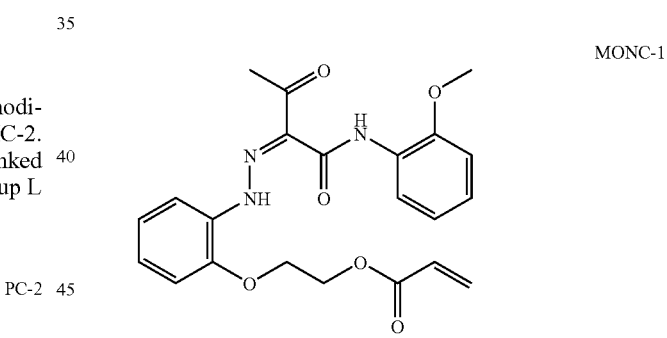

Ethylacetate (480 ml) was cooled to 0° C. Acrylic acid (19.0 g, 0.264 mol) and 2,6-di-tert-butyl-4-methylphenol (0.2 g, 0.00088 mol) were added. Triethylamine (26.7 g, 0.264 mol) was added drop-wise while the temperature was maintained between −5° C. and 0° C. Finally benzene sulfonyl chloride (22.3 g, 0.126 mol) was added drop-wise. Triethylamine hydrochloride precipitated. The reaction mixture was allowed to stir for 1 hour at 0° C. resulting in the formation of the symmetric anhydride. To this mixture N-hydroxysuccinimide (0.7 g, 0.006 mol) and MC-2 (22.3 g, 0.06 mol) were added at 5° C. The reaction mixture was refluxed (78° C.) for about 17 hours. The reaction mixture was diluted with EtOAc (100 ml) and extracted with distilled water (400 ml). The organic layer was separated and again extracted with a mixture of an aqueous solution of hydrochloric acid and distilled water (1/5). Finally the organic layer was washed with water and dried over $MgSO_4$. After evaporation of the solvent, the residue was suspended into distilled water and stirred for 45 minutes. Filtration provided a yellow solid.

Synthesis Scheme of MONC-1:

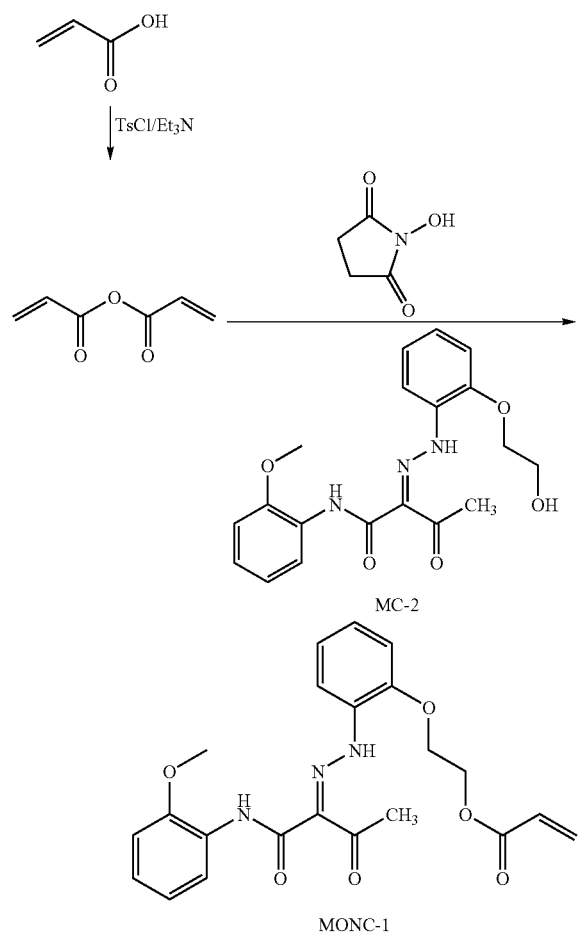

MC-2

MONC-1

Synthesis of Polymeric Dispersant DISP-3

The polymeric dispersant DISP-3 was prepared by copolymerizing the monomer MONC-1 with AA monomers in 90/10 molar ratio of AA/MONC-1.

The synthesis was performed in a 250 mL three-necked round-bottomed flask which was equipped with a cooling unit, a bubble counter on top and a stirring bar. 6.04 g of the monomer AA, 3.96 g of the monomer MONC-1, 0.43 g of the initiator WAKO™ V601, 0.44 g of the transfer agent MSTY were introduced in 89.13 g of dioxane. The total weight % concentration of the monomers was 10. The reaction mixture was degassed by bubbling nitrogen in the solution for approximately 30 min. The flask was immersed into an oil bath and heated to 80° C. and the mixture was further reacted for 20 hours. After polymerization, the reaction mixture was cooled down to room temperature. The polymer was precipitated in 1000 mL of water (acidified with HCl) and filtered off, followed by drying under vacuum at 40° C. for 24 hours to afford 8.4 g of yellow powder of DISP-3. (Yield=77.2%)

Analytical results of DISP-3: GPC: Mn=2745; Mw=5478; PD=2.00

(GPC in THF+5% acetic acid; calibrated vs. PS-standards)
NMR: AA/MONC-1 molar ratio was 90/10. On average DISP-3 contained 23.01 AA monomeric units and 2.55 MONC-1 monomeric units.

Synthesis of Polymeric Dispersant DISP-4

The polymeric dispersant DISP-4 was prepared by copolymerizing the monomer MONC-1 with AA monomers in 81/19 molar ratio of AA/MONC-1.

The synthesis was performed in a 250 mL three-necked round-bottomed flask which was equipped with a cooling unit, a bubble counter on top and a stirring bar. 4.04 g of the monomer AA, 5.96 g of the monomer MONC, 0.32 g of the initiator WAKO™ V601, 0.33 g of the transfer agent MSTY were introduced in 89.35 g of dioxane. The total weight % concentration of the monomers was 10. The reaction mixture was degassed by bubbling nitrogen in the solution for approximately 30 min. The flask was immersed into an oil bath and heated to 80° C. and the mixture was further reacted for 20 hours. After polymerization, the reaction mixture was cooled down to room temperature. The polymer was precipitated in 1000 mL of water (acidified with HCl) and filtered off, followed by drying under vacuum at 40° C. for 24 hours to afford 7.5 g of yellow powder of DISP-4. (Yield=70.4%)

Analytical results of DISP-4: GPC: Mn=1845; Mw=3187; PD=1.73

(GPC in THF+5% acetic acid; calibrated vs. PS-standards)
NMR: AA/MONC-1 molar ratio was 81/19. On average DISP-4 contained 10.73 AA monomeric units and 2.51 MONC-1 monomeric units.

Synthesis of Polymeric Dispersant DISP-5

The polymeric dispersant DISP-5 was prepared by copolymerizing the monomer MONC-1 with AA monomers in 71/29 molar ratio of AA/MONC-1.

The synthesis was performed in a 100 mL three-necked round-bottomed flask which was equipped with a cooling unit, a bubble counter on top and a stirring bar. 1.42 g of the monomer AA, 3.58 g of the monomer MONC-1, 0.21 g of the initiator WAKO™ V601, 0.22 g of the transfer agent MSTY were introduced in 44.57 g of dioxane. The total weight % concentration of the monomers was 10. The reaction mixture was degassed by bubbling nitrogen in the solution for approximately 30 min. The flask was immersed into an oil bath and heated to 80° C. and the mixture was further reacted for 20 hours. After polymerization, the reaction mixture was cooled down to room temperature. The polymer was precipitated in 500 mL of water (acidified with HCl) and filtered off, followed by drying under vacuum at 40° C. for 24 hours to afford 4.6 g of yellow powder of DISP-5. (Yield=84.7%)

Analytical results of DISP-5: GPC: Mn=2633; Mw=3982; PD=1.51

(GPC in THF+5% acetic acid; calibrated vs. PS-standards)
NMR: AA/MONC-1 molar ratio was 71/29. On average DISP-5 contained 10.71 AA monomeric units and 4.37 MONC-1 monomeric units.

Synthesis of Polymeric Dispersant DISP-6

The polymeric dispersant DISP-6 was prepared by copolymerizing the monomer MONC-1 with AA monomers in 55/45 molar ratio of AA/MONC-1.

The synthesis was performed in a 100 mL three-necked round-bottomed flask which was equipped with a cooling unit, a bubble counter on top and a stirring bar. 0.72 g of the monomer AA, 4.28 g of the monomer MONC, 0.21 g of the initiator WAKO™ V601, 0.22 g of the transfer agent MSTY were introduced in 44.57 g of dioxane. The total weight % concentration of the monomers was 10. The reaction mixture was degassed by bubbling nitrogen in the solution for approximately 30 min. The flask was immersed into an oil bath and heated to 80° C. and the mixture was further reacted for 20 hours. After polymerization, the reaction mixture was cooled down to room temperature. The polymer was precipitated in 500 mL of water (acidified with HCl) and filtered off, followed by drying under vacuum at 40° C. for 24 hours to afford 5 g of yellow powder of DISP-6. (Yield=92%)

Analytical results of DISP-6: GPC: Mn=2441; Mw=3458; PD=1.42

(GPC in THF+5% acetic acid; calibrated vs. PS-standards)

NMR: AA/MONC-1 molar ratio was 55/45. On average DISP-4 contained 5.81 AA monomeric units and 4.75 MONC-1 monomeric units.

Polymeric Dispersant DISP-7

A different monomer with chromophore group, MONC-2, was used to prepare polymeric dispersant DISP-7.

Synthesis of the Monomer MONC-2

Synthesis Scheme:

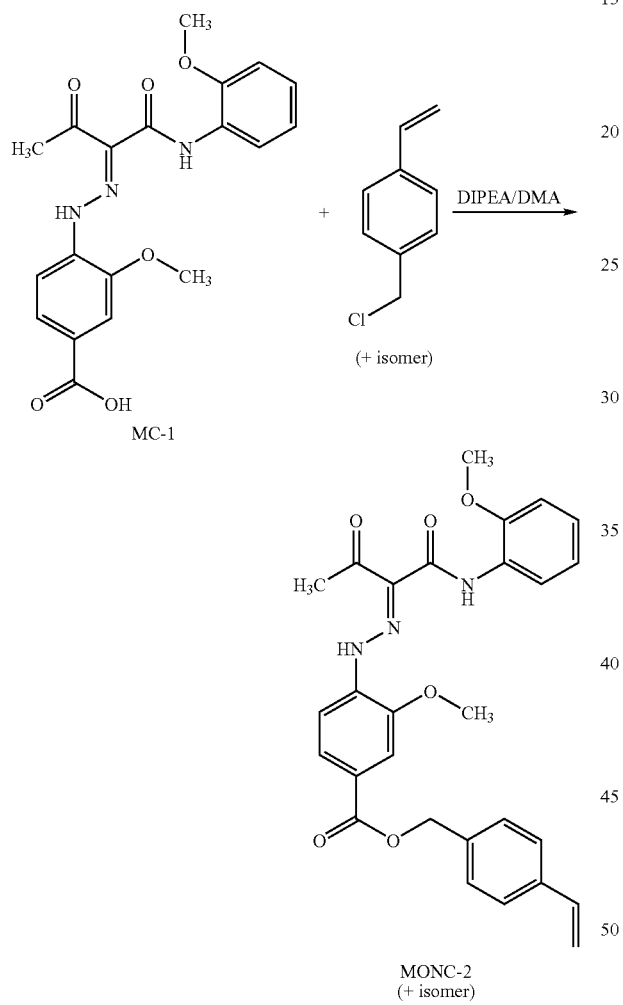

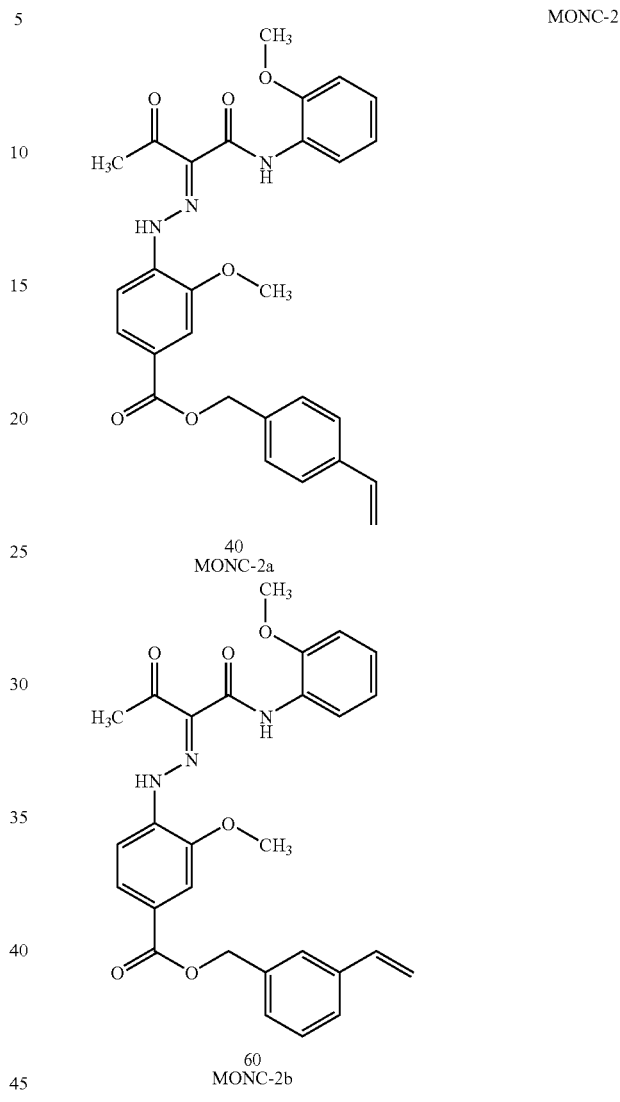

12.6 g (0.03 mol) of MC-1 was dissolved in 660 ml dimethylacetamide. The mixture was heated to 70° C. and allowed to cool down to 60° C. 4.7 g (0.036 mol) diisopropyl-ethyl-amine was added and the mixture was allowed to cool down to 40° C. Then 5.7 g (0.036 mol) of chloromethylstyrene (mixture of isomers) was added and the mixture was heated to 70° C. The reaction was allowed to continue for 12 hours at 70° C. The reaction mixture was cooled to −10° C. and 100 ml water was added in portions of 20 ml. The mixture was stirred for 30 minutes at −10° C. The monomer MONC-2 precipitated from the medium. The monomer was isolated by filtration and dried with a yield of 81%. The structure was confirmed using LC-MS. MONC-2 was a 40/60 mixture of the two monomers MONC-2a (linked in para position) and MONC-2b (linked in meta position).

Synthesis of Polymeric Dispersant DISP-7

The polymeric dispersant DISP-7 was prepared by copolymerizing the monomer MONC-2 with AA monomer.

The synthesis was performed in a 100 ml three-necked round-bottomed flask which was equipped with a cooling unit, a bubble counter on top, and a stirring bar. 2.26 g of the monomer AA, 1.74 g of the monomer MONC-2, 0.12 g of the initiator WAKO™ V601, 0.12 g of the transfer agent MSTY were introduced in 35.76 g of dioxane. The total weight % concentration of the monomers was 10. The reaction mixture was degassed by bubbling nitrogen in the solution for approximately 30 min. The flask was immersed into an oil bath and heated to 80° C. and the mixture was further reacted for 20 hours. After polymerization, the reaction mixture was cooled down to room temperature. The polymer was precipitated in 500 ml of water (acidified with HCl) and filtered off, followed by drying under vacuum at 40° C. for 24 hours to afford 3 g of yellow powder of DISP-7. The yield was 71%.

Analytical results of DISP-7: GPC: Mn=1999; Mw=3945; PD=1.97

(GPC in THF+5% acetic acid; calibrated vs. PS-standards)

NMR: AA/MONC-2 molar ratio was 86/4. On average DISP-7 contained 13 AA monomeric units and 2 MONC-2 monomeric units.

Preparation of Inkjet Ink

All inkjet inks were prepared in the same manner to obtain a composition as described in Table 6, except that different pigments and dispersants were used.

TABLE 6

| Component | wt % |
|---|---|
| Pigment | 4.00 |
| Dispersant | 2.40 |
| 1,2-propanediol | 21.00 |
| Glycerol | 7.00 |
| Proxel ™ Ultra 5 | 0.80 |
| Surfynol ™ 104H | 0.09 |
| Water | 64.71 |

An ink composition was made by mixing the pigment, the dispersant and about half of the water with a dissolver and subsequently treating this mixture with a roller mill procedure using yttrium-stabilized zirconium oxide-beads of 0.4 mm diameter ("high wear resistant zirconia grinding media" from TOSOH Co.). A polyethylene flask of 60 mL was filled to half its volume with grinding beads and 20 g of the mixture. The flask was closed with a lid and put on the roller mill for three days. The speed was set at 150 rpm. After milling, the dispersion was separated from the beads using a filter cloth. During stirring, the surfactant Surfynol™ 104H and the biocide Proxel™ Ultra 5, glycerol, 1,2-propanediol and the remaining water were added. This mixture was stirred for 10 minutes and filtered. The filtration was performed in two steps. First, the ink mixture is filtered using a (plastipak) syringe with a microfiber disposable filtercapsule with 1 μm pore diameter (GF/B microfiber from Whatman Inc.) Then the same procedure is repeated on the filtrate. After the second filtration the ink is ready for evaluation.

Using the above method, the comparative inkjet inks COMP-1 to COMP-4 and the inventive inkjet inks INV-1 to INV-9 were prepared according to Table 7.

TABLE 7

| Inkjet Ink | Polymeric Dispersant | Monomer | Color Pigment |
|---|---|---|---|
| COMP-1 | DISP-1 | — | PY74 |
| COMP-2 | DISP-1 | — | PY17 |
| COMP-3 | DISP-2 | — | PY74 |
| COMP-4 | DISP-2 | — | PY17 |
| INV-1 | DISP-3 | MONC-1 | PY74 |
| INV-2 | DISP-3 | MONC-1 | PY17 |
| INV-3 | DISP-4 | MONC-1 | PY74 |
| INV-4 | DISP-4 | MONC-1 | PY17 |
| INV-5 | DISP-5 | MONC-1 | PY74 |
| INV-6 | DISP-5 | MONC-1 | PY17 |
| INV-7 | DISP-6 | MONC-1 | PY74 |
| INV-8 | DISP-6 | MONC-1 | PY17 |
| INV-9 | DISP-7 | MONC-2 | PY17 |

Results and Evaluation

The spectral separation factor (SSF) was determined for each sample directly after preparation. The results are listed in Table 8 together with the % MW.

TABLE 8

| Inkjet Ink | Monomer | Chromophore Group | Color Pigment | % MW | SSF |
|---|---|---|---|---|---|
| COMP-1 | — | None | PY74 | 0 | 2 |
| COMP-2 | — | None | PY17 | 0 | 0 |
| COMP-3 | — | Yes | PY74 | 81 | 196 |
| COMP-4 | — | Yes | PY17 | 45 | 79 |
| INV-1 | MONC-1 | Yes | PY74 | 81 | 292 |
| INV-2 | MONC-1 | Yes | PY17 | 45 | 234 |
| INV-3 | MONC-1 | Yes | PY74 | 81 | 310 |
| INV-4 | MONC-1 | Yes | PY17 | 45 | 245 |
| INV-5 | MONC-1 | Yes | PY74 | 81 | 234 |
| INV-6 | MONC-1 | Yes | PY17 | 45 | 254 |
| INV-7 | MONC-1 | Yes | PY74 | 81 | 27 |
| INV-8 | MONC-1 | Yes | PY17 | 45 | 197 |
| INV-9 | MONC-2 | Yes | PY17 | 56 | 194 |

From Table 8 it is clear that the polyacrylic acid homopolymer was incapable of dispersing the pigments PY74 and PY17 in the comparative inkjet inks COMP-1 and COMP-2. Modification of the polyacrylic acid with a chromophore results already in high SSF values for the comparative inkjet inks COMP-3 and COMP-4. However, the highest SSF values were obtained when using polymeric dispersants prepared by copolymerizing monomers having a chromophore group in the inventive inkjet inks INV-1 to INV-9 with the exception of inventive inkjet ink INV-7. The inventive inkjet ink INV-7 shows that there is an upper-limit for the number of monomers with a chromophore group in the polymeric dispersant, as the dispersion quality was reduced to an unacceptable level for pigment PY74.

The simple method of copolymerizing a monomer already containing a small chromophore group offers the advantage of well controlled design and synthesis of polymeric dispersants for one or more pigments for a specific dispersion medium.

Example 2

This example illustrates the improved thermal stability of inkjet inks using a polymeric dispersant prepared by the method of copolymerizing a monomer already containing a small chromophore group. It also illustrates the advantage that a monomer with a chromophore group allows the well controlled design and synthesis of polymeric dispersants.

Polymeric Dispersant DISP-8

The polymeric dispersant DISP-8 was prepared by copolymerizing the monomer MONC-1 with AA and BA monomers.

Synthesis of Polymeric Dispersant DISP-8

The synthesis was performed in a 50 ml three-necked round bottomed flask which was equipped with a cooling unit, a bubble counter on top, and a stirring bar. 1.47 g of the monomer AA, 2.61 g of the monomer BA, 1.93 g of the monomer MONC-1, 0.20 g of the initiator WAKO™ V601, 0.21 g of the transfer agent MSTY were introduced in 23.59 g of MEK. The total weight % concentration of the monomers was 20. The reaction mixture was degassed by bubbling nitrogen in the solution for approximately 30 min. The flask was immersed into an oil bath and was heated to 80° C. and the mixture was further reacted for 20 hours. After polymerization, the reaction mixture was cooled down to room temperature. The polymer was precipitated in 250 ml of water followed by drying under vacuum at 40° C. for 24 hours to afford 3.32 g of yellow powder of DISP-8. (Yield=51.8%)

Analytical results of DISP-8: GPC: Mn=5875; Mw=10853; PD=1.85 (GPC in THF+5% acetic acid; calibrated vs. PS-standards)

NMR: AA/BA/MONC-1 molar ratio was 47/43/10. On average DISP-8 contains 21 AA monomeric units, 19 BA monomeric units and 4 MONC-1 monomeric units.

Polymeric Dispersant DISP-9

The polymeric dispersant DISP-9 was prepared by copolymerizing the monomer MONC-3 with MAA and EHA monomers.

Synthesis of Chromophore MC-3

Preparation of Compound MC-8B

The vessel used to carry out this reaction was a 3 necked flask equipped with a stirrer, a cooler, and a dropping-funnel. To a solution of 140 g (1 mol) 3-nitrophenol (compound MC-8A) and 1.4 L N-methylpyrolidone was added 190 mL sodium methylate 30% (1.025 mol). The mixture was distillated at a temperature of 100° C. and 80 mbar pressure. After the distillation 87 mL (1.3 mol) of 2-chloroethanol (compound MC-1B) was added dropwise. After addition of the 2-chloroethanol, the mixture was heated to a temperature of about 120° C. for 3 hours. The reaction mixture was poured into 6 L of water with 85 mL HCl conc. The product was filtrated. The yield of compound MC-8B was 27%.

Synthesis Scheme of Compound MC-8B:

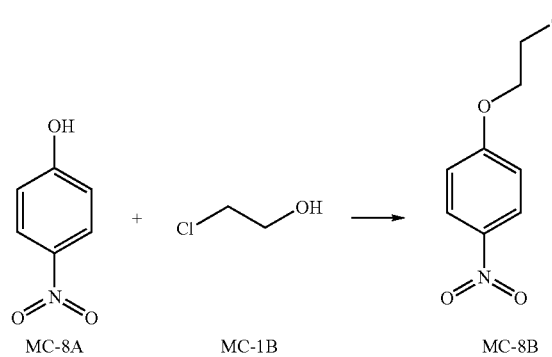

Preparation of Compound MC-8C

Compound MC-8C was made by catalytic reduction of compound MC-8B with hydrogen.

A reactor was filled with 101 g (0.55 mol) of compound MC-8B in 700 mL ethanol and 11 mL of Raney Nickel™ slurry was added. The reduction was carried out at a starting temperature of 75° C. under an initial $H_2$-pressure of 46 bar. After reduction, the charge was mixed during 1 hour and the Raney Nickel™ was filtered off. The filtrate was evaporated at a temperature of 50° C. until the desired white crystalline product MC-8C appeared. The yield of compound MC-8C was 95%.

Synthesis Scheme of Compound MC-8C:

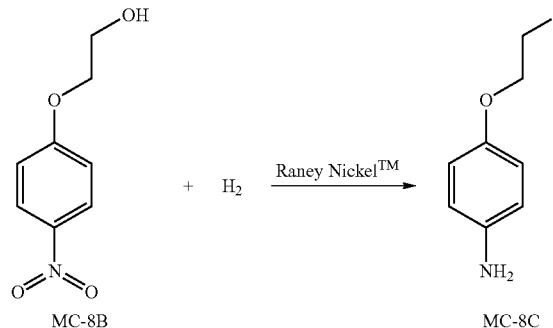

Preparation of Compound MC-3

6.9 g (45.2 mmol) of compound MC-8C was mixed with 40 mL $H_2O$ and 10 mL methanol. Then, 4.5 g (54 mmol) of compound MC-1F was added and the mixture was stirred for 30 minutes. This is mixture A-MC-3. 6.2 g (45.2 mmol) of compound MC-3A was added to 100 mL of $H_2O$. 16.2 g (162 mmol) of concentrated HCl was added. The solution was cooled to a temperature of about 0° C. to 5° C. 4.05 g (58.8 mmol) of sodium nitrite was added and the mixture was kept at a temperature between 0° C. and 5° C. After 15 minutes, the excess of nitrite was neutralized by adding 1.36 g (13.6 mmol) of sulfamic acid and a pH of 7 was obtained by adding 11.4 g (136 mmol) of sodium carbonate. The mixture A-MC-3 was added and the mixture was stirred for 1 hour at a temperature between 0° C. and 5° C. The stirring was continued for 1 hour at a temperature between 0° C. and 5° C. The yellow product was filtered and washed with methanol. The yield of the chromophore MC-3 was 87%.

Synthesis Scheme:

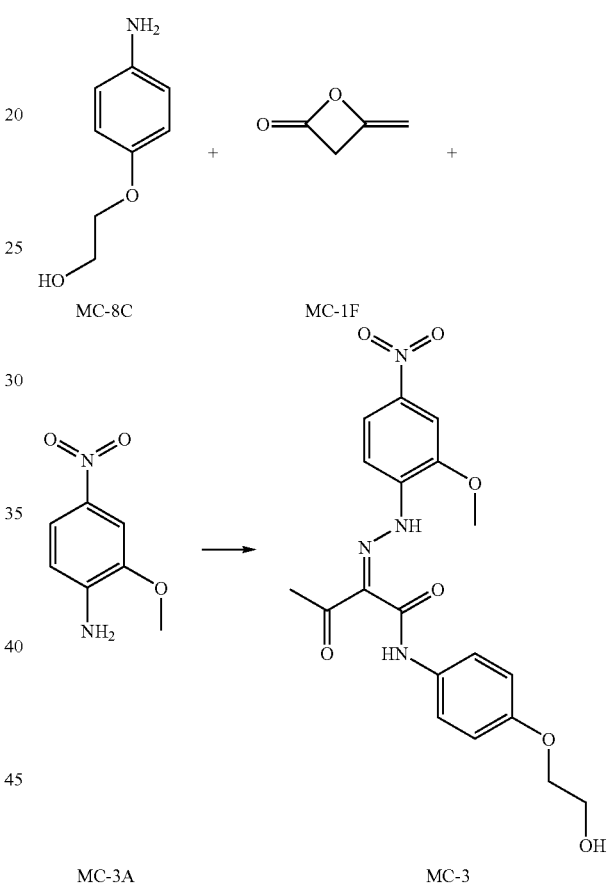

Synthesis of the Monomer MONC-3

Synthesis Scheme:

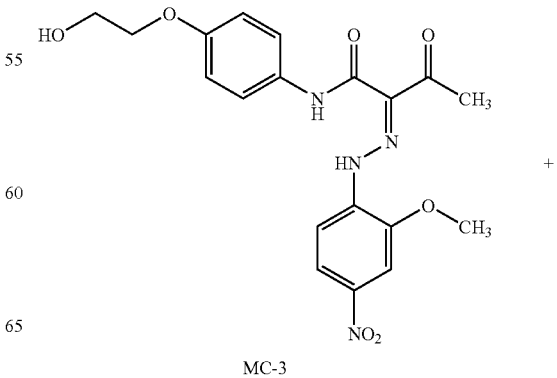

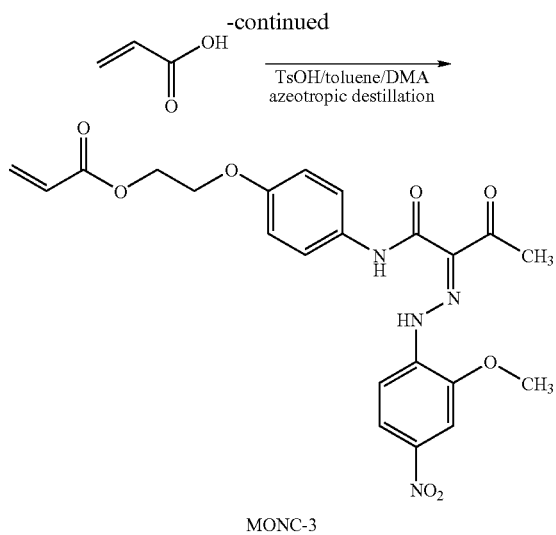

MONC-3

1.2 g (16 mmol) acrylic acid, 6.7 g of chromophore MC-3 and 3.0 g p.-toluene sulfonic acid monohydrate were dissolved in 200 ml toluene and 20 ml dimethylacetamide. The mixture was refluxed under azeotropical removal of water for 16 hours. The mixture was allowed to cool down to room temperature, The undissolved residues were removed by filtration. The solvents were removed under reduced pressure. The residue was suspended in 300 ml methyl-t.butyl-ether and refluxed for 2 hours. The mixture was allowed to cool down to room temperature and the crude monomeric dye was isolated by filtration and dried. The crude product was purified by preparative column chromatography on a Varian Mega bond 70 g, using methylene chloride as eluent. 1.78 g of the purified dye was isolated. The yield was 24%.

Synthesis of Polymeric Dispersant DISP-9

The synthesis was performed in a 50 ml three-necked round-bottomed flask which was equipped with a cooling unit, a bubble counter on top, and a stirring bar. 1.38 g of the monomer MAA, 2.95 g of the monomer EHA, 1.67 g of the monomer MONC-3, 0.20 g of the initiator WAKO™ V601, 0.21 g of the transfer agent MSTY were introduced in 23.59 g of MEK. The total weight % concentration of the monomers was 20. The reaction mixture was degassed by bubbling nitrogen in the solution for approximately 30 min. The flask was immersed into an oil bath and heated to 80° C. and the mixture was further reacted for 20 hours. After polymerization, the reaction mixture was cooled down to room temperature. The polymer was precipitated in 250 ml of water and filtered off, followed by drying under vacuum at 40° C. for 24 hours to afford 4.1 g of yellow powder of DISP-9. The yield was 64%.

Analytical results of DISP-9: GPC: Mn=6235; Mw=11654; PD=1.87

(GPC in THF+5% acetic acid; calibrated vs. PS-standards)

NMR: MAA/EHA/M0NC-3 molar ratio was 51/45/4. On average DISP-9 contained 22 MAA monomeric units, 19 EHA monomeric units and 2 M0NC-3 monomeric units.

Preparation of Inkjet Inks

The inventive inkjet inks INV-11 and INV-12 were prepared in the same manner as the comparative inkjet ink COMP-3 and the inventive inkjet inks INV-1, INV-3, INV-5, and INV-10 in EXAMPLE 1 using the color pigment PY74 and the polymeric dispersants according to Table 9.

TABLE 9

| Inkjet Ink | Polymeric Dispersant | Monomer | Other Monomers |
|---|---|---|---|
| COMP-3 | DISP-2 | No | AA |
| INV-1 | DISP-3 | MONC-1 | AA |
| INV-3 | DISP-4 | MONC-1 | AA |
| INV-5 | DISP-5 | MONC-1 | AA |
| INV-10 | DISP-7 | MONC-2 | AA |
| INV-11 | DISP-8 | MONC-1 | AA/BA |
| INV-12 | DISP-9 | MONC-3 | MAA/EHA |

Results and Evaluation

The spectral separation factor (SSF) was determined for each sample directly after preparation and was determined again after a severe heat treatment of 1 week at 80° C. The results are listed in Table 10.

TABLE 10

| Inkjet Ink | Monomer | SSF | SSF 1 week/80° C. |
|---|---|---|---|
| COMP-3 | No | 196 | 76 |
| INV-1 | MONC-1 | 292 | 114 |
| INV-3 | MONC-1 | 310 | 258 |
| INV-5 | MONC-1 | 234 | 244 |
| INV-10 | MONC-2 | 229 | 225 |
| INV-11 | MONC-1 | 302 | 291 |
| INV-12 | MONC-3 | 318 | 323 |

From Table 10 it is clear that the inventive pigmented inkjet inks INV-1, INV-3, INV-5, INV-10, INV-11, and INV-12 were capable of dispersing the color pigment C.I. Pigment Yellow 74 with high dispersion quality and improved dispersion stability compared to the comparative inkjet ink COMP-3 where the polymeric dispersant had been modified with a similar chromophore.

While preferred embodiments of the present invention have been described above, it is to be understood that variations and modifications will be apparent to those skilled in the art without departing the scope and spirit of the present invention. The scope of the present invention, therefore, is to be determined solely by the following claims.

The invention claimed is:

1. A monomer with a chromophore group represented by Formula (I):

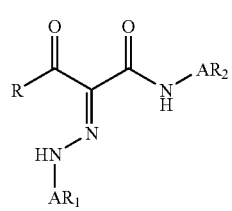

Formula (I)

wherein
 AR$_1$ represents a substituted or unsubstituted aromatic group;
 AR$_2$ represents a substituted or unsubstituted aromatic group or a substituted or unsubstituted alkyl group; and
 R represents a substituted or unsubstituted alkyl group, with the proviso that one of R, AR$_1$, and AR$_2$ has a substituent with a polymerizable functional group selected from the group consisting of a styrene group, an acrylate group, a methacrylate group, a maleimide group, a vinyl ester group, and a vinyl ether group.

2. The monomer according to claim 1, wherein the polymerizable functional group is an acrylate group or a methacrylate group.

3. The monomer according to claim 1, wherein $AR_2$ represents methyl or ethyl.

4. The monomer according to claim 2, wherein $AR_2$ is selected from the group consisting of

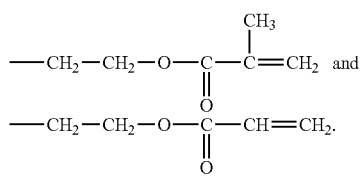

5. The monomer according to claim 1 represented by Formula (II):

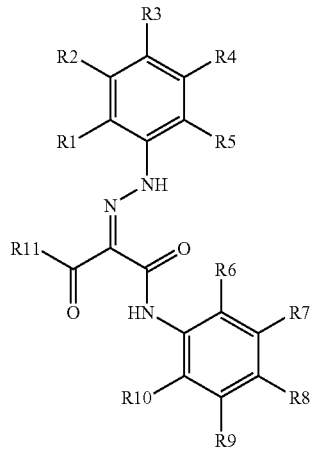

Formula (II)

wherein
one of R1 to R11 is the substituent with and said polymerizable functional group;
R1 to R6, R9, and R10, if not representing the substituent with a polymerizable functional group, are independently selected from the group consisting of hydrogen, an alkyl group, an alkenyl group, an alkoxy group, an alcohol group, a carboxylic acid group, an ester group, an acyl group, a nitro group, and a halogen;
R7 and R8, if not representing the substituent with and said polymerizable functional group and not independently selected from the group consisting of hydrogen, an alkyl group, an alkenyl group, an alkoxy group, an alcohol group, a carboxylic acid group, an ester group, an acyl group, a nitro group, and a halogen; together form a heterocyclic ring; and
R11 if not representing the substituent with said polymerizable functional group, represents a substituted or unsubstituted alkyl group.

6. The monomer according to claim 5, wherein the heterocyclic ring formed by R7 and R8 is imidazolone or 2,3-dihydroxypyrazine.

7. The monomer according to claim 1 selected from the group consisting of:

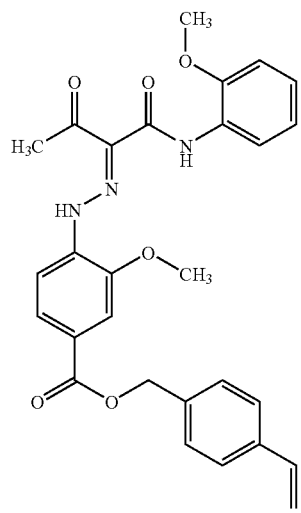

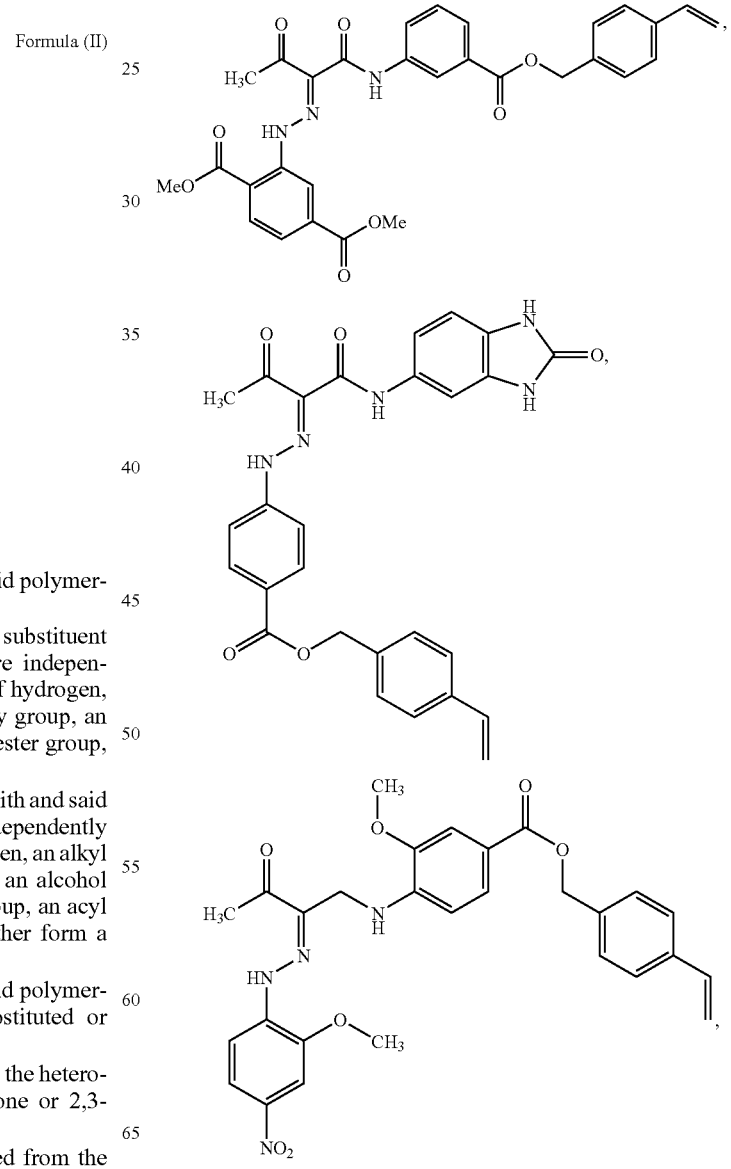

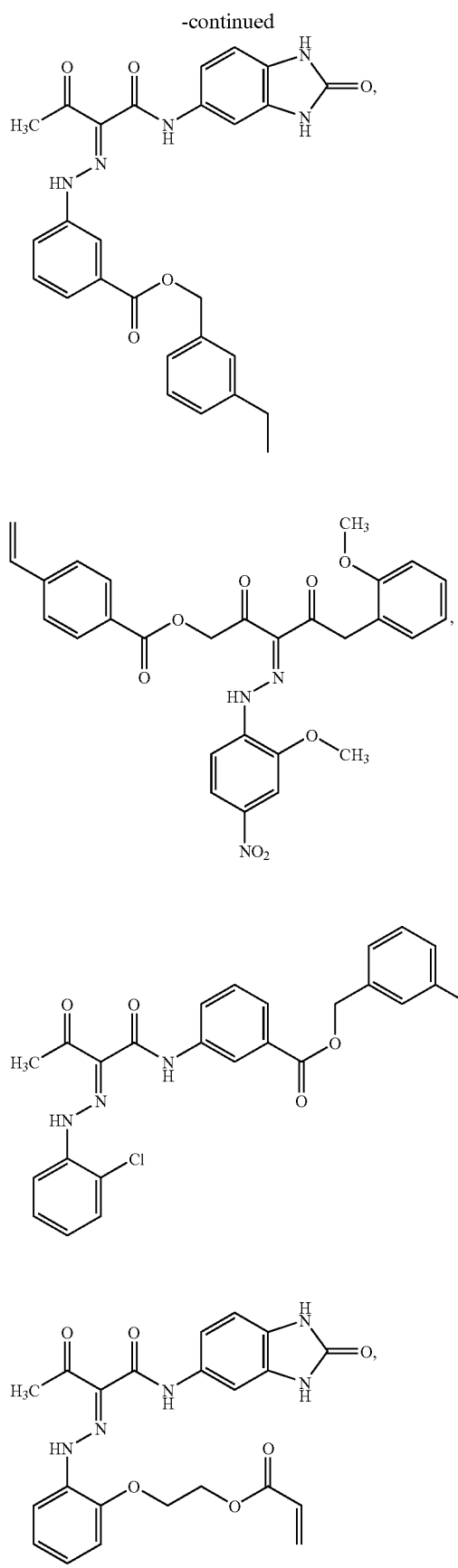

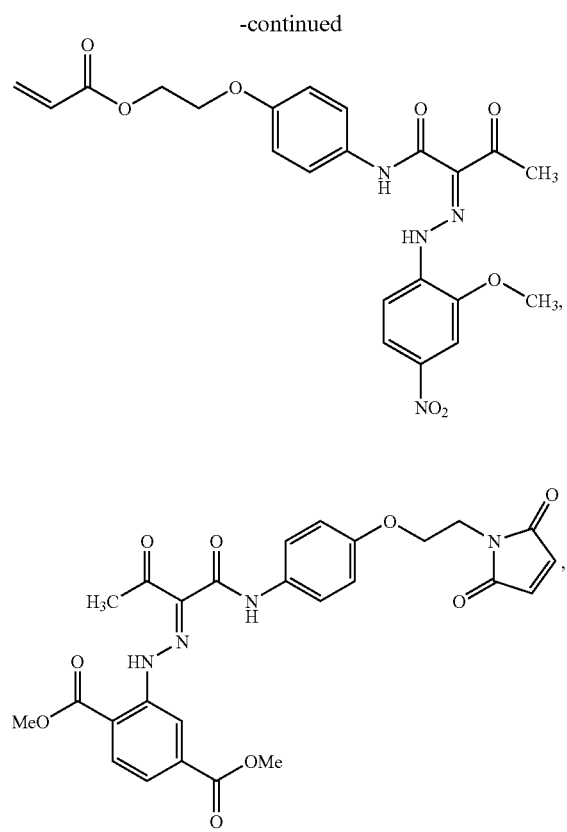
8. A polymer comprising the monomer of claim 1.
9. A radiation curable pigment dispersion comprising the monomer of claim 1.
10. A radiation curable inkjet ink comprising the monomer of claim 1.
* * * * *